United States Patent [19]
Kaufman et al.

[11] Patent Number: 5,267,174
[45] Date of Patent: Nov. 30, 1993

[54] INTERACTIVE MEDICATION DELIVERY SYSTEM

[75] Inventors: Stephen B. Kaufman, Highland Park; Aleandro DiGianfilippo, Crystal Lake; Tamara L. Sager, Libertyville, all of Ill.

[73] Assignee: HealthTech Services Corp., Northbrook, Ill.

[21] Appl. No.: 877,695

[22] Filed: May 1, 1992

Related U.S. Application Data

[60] Division of Ser. No. 747,648, Aug. 20, 1991, Pat. No. 5,126,957, which is a continuation of Ser. No. 415,172, Sep. 29, 1989, Pat. No. 5,084,828.

[51] Int. Cl.$^5$ ............... G06F 15/42; B65D 83/04
[52] U.S. Cl. ............... 364/479; 364/413.02; 221/2; 221/9; 395/2
[58] Field of Search ............ 364/479, 413.02, 413.03, 364/413.04, 569; 221/2-9, 15, 197; 128/630; 368/10; 395/2

[56] References Cited

U.S. PATENT DOCUMENTS

| | | | |
|---|---|---|---|
| 4,572,403 | 2/1986 | Benaroya | 364/479 X |
| 4,695,954 | 9/1987 | Rose et al. | 364/479 X |
| 4,733,362 | 3/1988 | Haraguchi | 364/479 |
| 4,785,969 | 11/1988 | McLaughlin | 364/479 X |
| 4,839,806 | 6/1989 | Goldfischer et al. | 364/413.02 |
| 4,847,764 | 7/1989 | Halvorson | 364/479 X |
| 4,933,873 | 6/1990 | Kaufman et al. | 395/2 |
| 4,970,669 | 11/1990 | McIntosh et al. | 364/569 |

Primary Examiner—Joseph Ruggiero
Attorney, Agent, or Firm—Ryan, Kees & Hohenfeldt

[57] ABSTRACT

A medication delivery device includes a housing containing separate first and second storage locations for holding medication dosages away from access by the user. Associated separate first and second delivery mechanisms permit selective delivery of a medication dose from either the first or second storage locations to the patient. The invention provides a control element that discriminates between the actuation of the first delivery mechanism and the second delivery mechanism, thereby discriminating between the delivery of medication housed in the first and second storage locations. The control element discriminates between different first and second input criteria. In response to the first input criteria but not in response to the second input criteria, the control element actuates the first delivery mechanism. In response to the second input criteria, the control element actuates the second delivery mechanism.

7 Claims, 23 Drawing Sheets

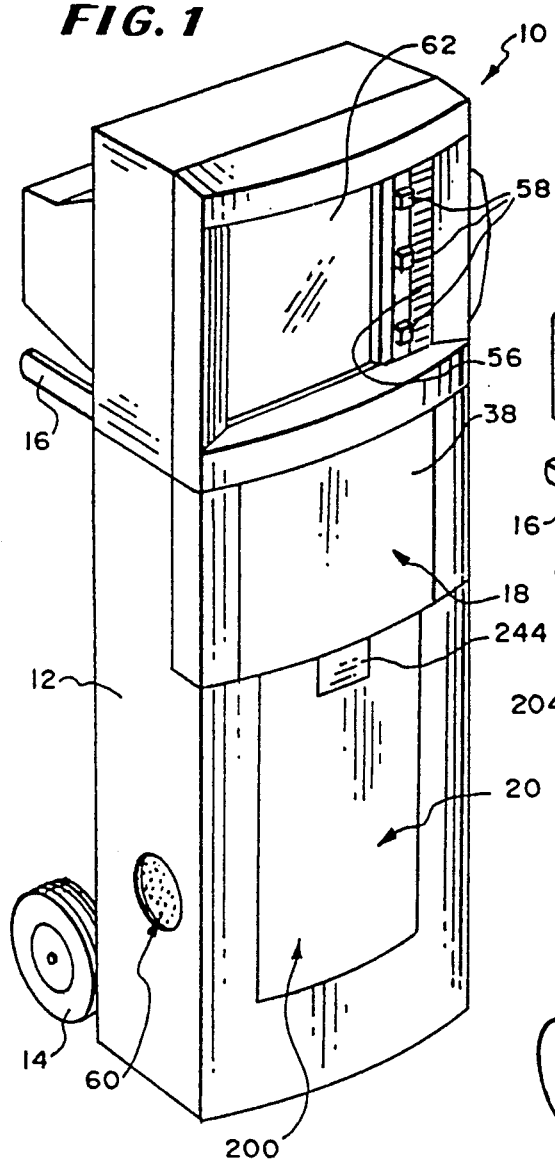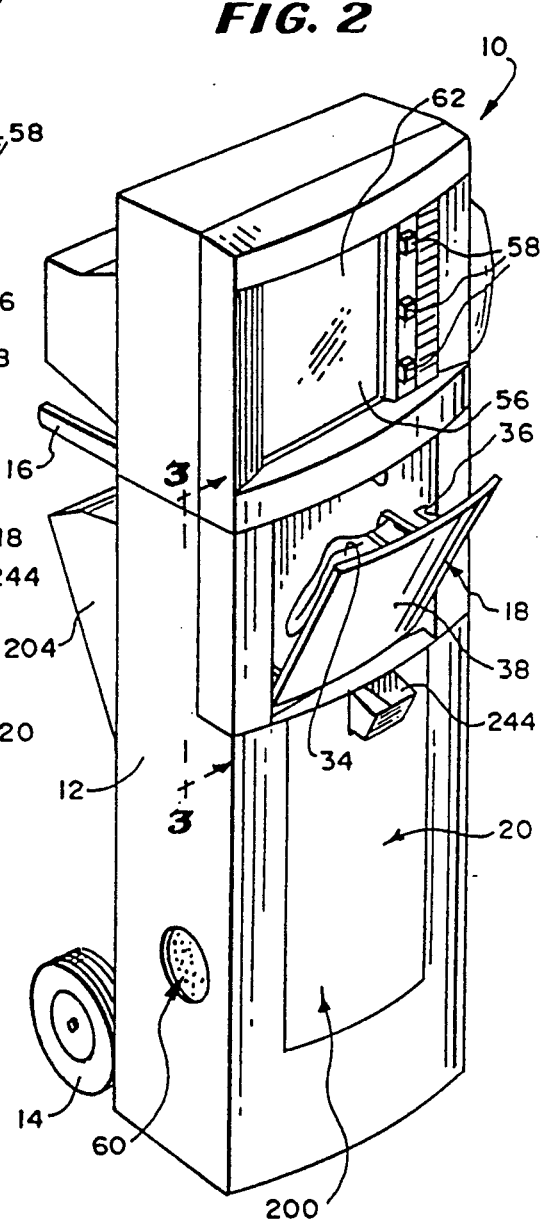

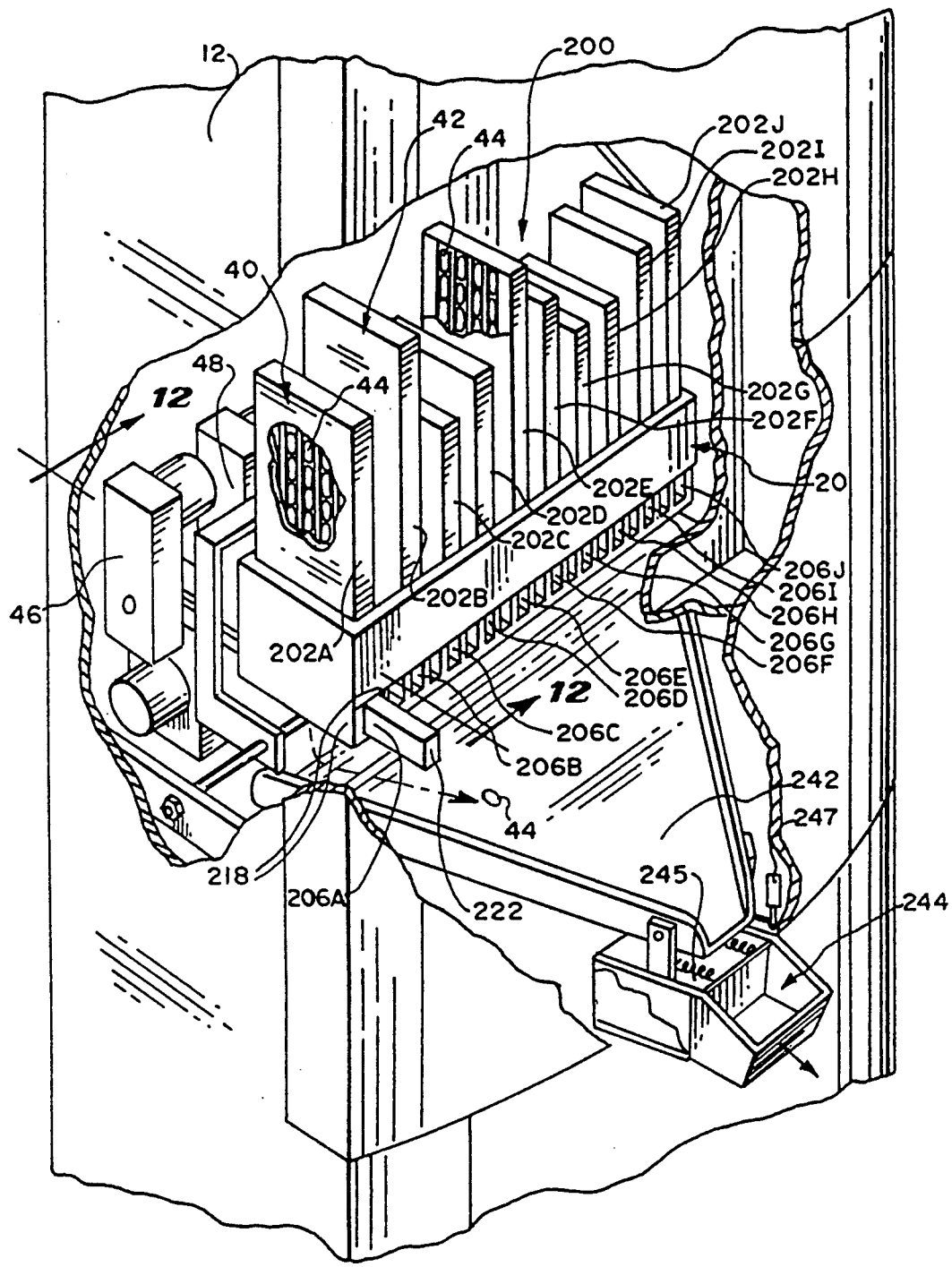

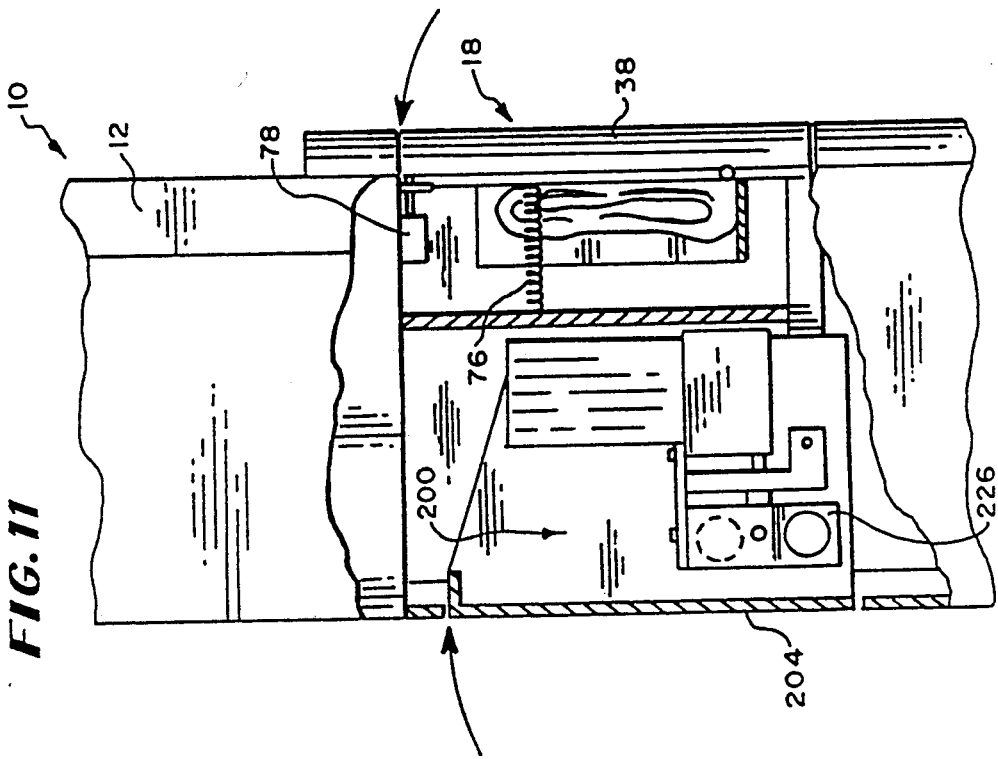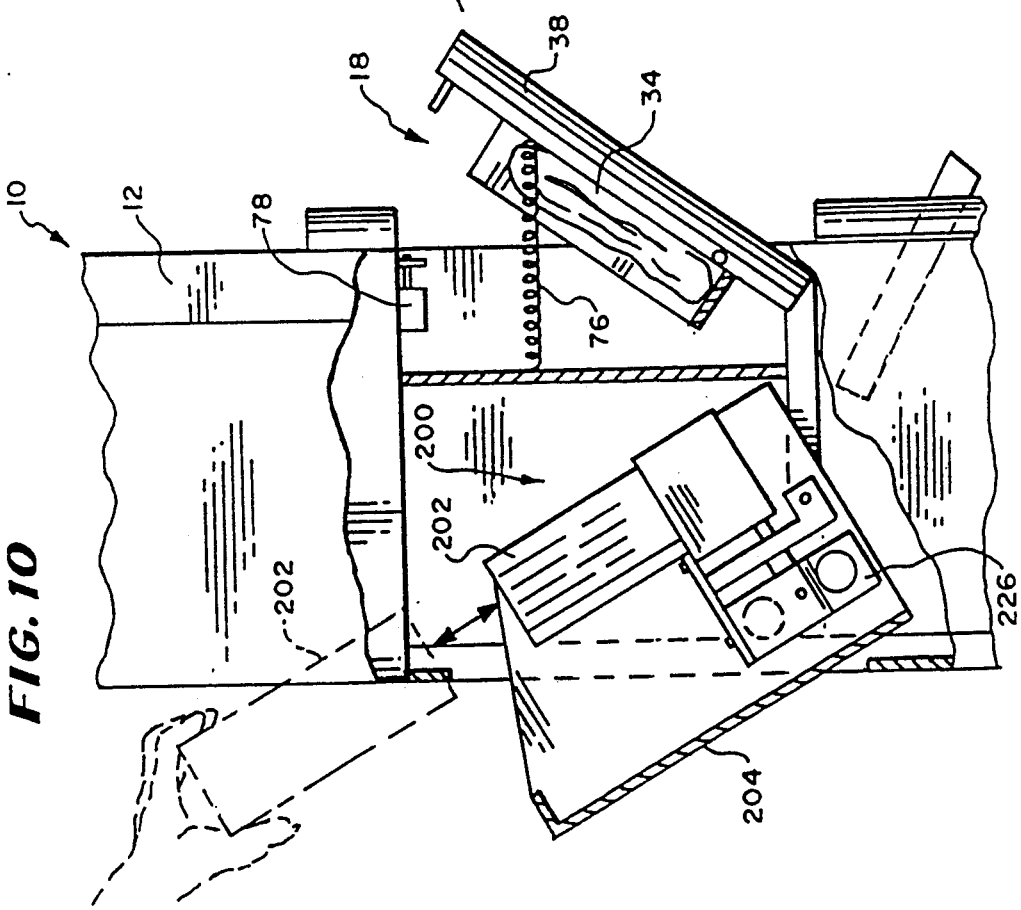

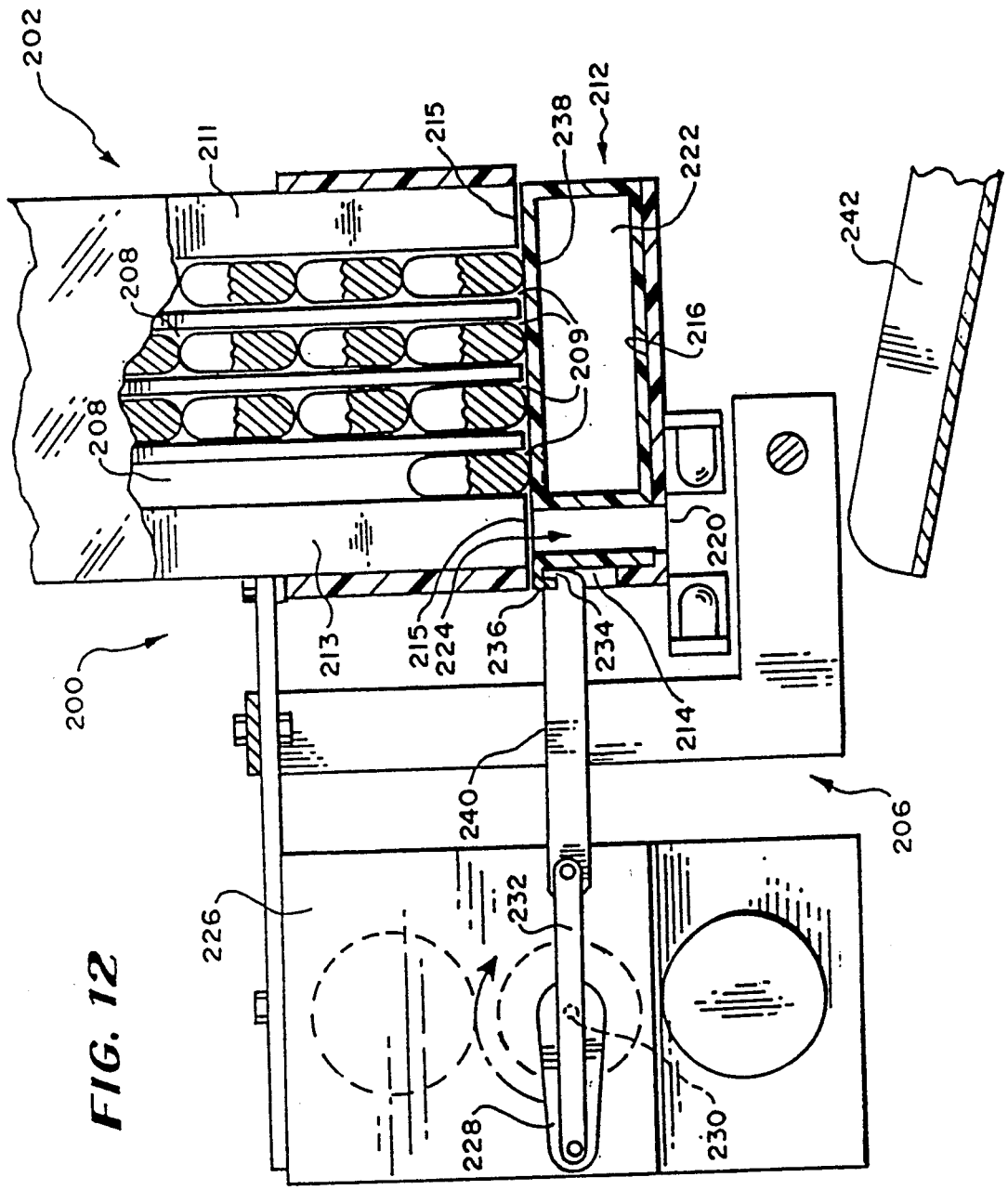

INTERACTIVE MEDICATION DELIVERY SYSTEM

This is a divisional of copending application Ser. No. 07/747,648 filed on Aug. 20, 1991 (now U.S. Pat. No. 5,126957), which is a continuation of application Ser. No. 07/415,172 filed on Sep. 29, 1989 (now U.S. Pat. No. 5,084,828 issued Jan. 28, 1992).

FIELD OF THE INVENTION

The invention generally relates to systems for dispensing medications. In a more particular sense, the invention concerns systems which oversee and coordinate the administration of complex medication regimens at home, outside the support system of a hospital or pharmacy, and without the day to day supervision of medical personnel. In this more particular sense, the invention also concerns automated home care patient health monitoring systems.

BACKGROUND OF THE INVENTION

Due to advances in medicine and medical treatments in general, people are living longer. As a result, the number and percentage of older people are growing in the United States and elsewhere.

However, despite medical advances, many elderly people still face chronic and debilitating health problems. Arthritis, hypertension, and heart conditions are but a few examples of the problems associated with longevity.

Treatment of these health problems often requires close compliance with relatively complex medication regimes. It is not unusual for a person having one of the above health problems to be taking four or more different prescription drugs at one time. These drugs often differ significantly in dosages, both as to time and amount, as well as in their intended physiological effects. These drugs also often differ in the severity of potentially adverse reactions due to mismedication.

Close and careful compliance with these complex medication regimes is a difficult task in itself. The difficulty is greatly enhanced, considering that the - elderly must discipline themselves to follow these regimes at home, without the day-to-day support and supervision of trained hospital and pharmacy personnel, and often without the day-to-day support and supervision of their immediate families or other caregivers. Furthermore, a loss in short term memory can be naturally attributed to the aging process and to the medication themselves, resulting in forgetfulness and further confusion in scheduling compliance with complicated medication regimes.

The elderly are therefore increasingly at risk of hospitalization or death from mismedication.

An interactive patient assistance device, ideally suited to the needs of home care patients—young and old alike—is described in Kaufman et al. U.S Pat. Application 201,779 (filed Jun. 2, 1988), now U.S. Pat. No. 4,933,873. The device includes a self-contained medication delivery mechanism and self-contained physical testing apparatus. The device normally retains the medication and the testing apparatus away from access by the patient. Both medication and the testing apparatus are made available to the patient, either in response to a prescribed schedule or in response to a verbal command made by the patient.

The present invention enhances and expands the flexible, interactive system described in the Kaufman et al. application.

The invention is directed to improving the overall well-being and lifestyle of home care patients who are on complicated medication regimes. The invention addresses the problems of compliance with a complicated regime of differing medications and solves these problems by providing a reasonable degree of self-sufficiency and personal control over the administration of medication without sacrificing the overall therapeutic objectives of the prescribed medical treatment.

SUMMARY OF THE INVENTION

The invention provides an interactive medication delivery device that discriminates, within a given medication regime, between different categories of medication and different schedules of medication administration. The invention provides a device that can administer medication differently, realizing that a given treatment regime often involves the administration of altogether different types of medication. The invention provides a significant degree of flexibility that permits a patient to exercise greater personal control over the administration of his or her medication. However, at the same time, the invention assures strict adherence to a prescribed medication regime.

The medication delivery device that embodies the features of the invention includes a housing containing separate first and second storage locations for holding medication dosages away from access by the patient. Associated separate first and second delivery mechanisms permit selective delivery of a medication dose from either the first or second storage locations to the patient. The invention provides a control element that discriminates between the criteria for actuating the first deliver mechanism and the criteria for actuating the second delivery mechanism. The control element thereby discriminates between the delivery of medication housed in the first and second storage locations.

In one aspect of the invention, the different input criteria discriminate between one category of medication that can be only administered according to a prescribed schedule and another category of medication that can be safely administered upon demand. In this aspect, the control element includes internal memory for storing the prescribed medication administration schedule, as well as an external input device for receiving and interpreting at least one prescribed medication delivery command from the patient. In this arrangement, the control element actuates the first delivery mechanism in response to the prescribed schedule stored in the internal memory, but it will not actuate the first delivery mechanism in response to the receipt of a medication delivery command from the external input device. The medication that is to be administered only in response to the prescribed schedule can thereby be placed in the first storage location, and the device will assure compliance by delivering it to the patient only in accordance with the schedule. However, the control element will actuate the second delivery mechanism in response to the receipt of a prescribed medication delivery command from the patient via the external input device. The medication that can be delivered upon patient demand can thereby be placed in the second storage location, separate from the other, more strictly controlled medication. The control element will allow the patient access to the permitted "on demand" medication, without otherwise jeopardizing the rest of the patient's medication regime.

In another aspect of the invention, the different input criteria discriminate between categories of medication that are administered according to different prescribed schedules. In this arrangement, the control element actuates the first delivery mechanism in response to a first prescribed schedule, but not in response to a second prescribed schedule. The control element responds to the second prescribed schedule to actuate the second delivery mechanism.

In one embodiment of this arrangement, the control element includes an external input for receiving and interpreting at least one prescribed medication delivery command from the patient, as before described. In this embodiment, control element actuates the first delivery mechanism as before described, in response to the first prescribed schedule, but not in response to either the second prescribed schedule or the medication delivery command from the external input. However, control element will actuate the second delivery mechanism not only in response the second prescribed schedule but also in response to a prescribed medication delivery command from the external input. Therefore, the invention will flexibly accommodate a medication that is be administered in accordance with a schedule, but that can also be administered upon demand by the patient.

In another aspect of the invention, the different input criteria discriminate between one category of medication that can be only administered according to the schedule prescribed by the physician and another category of medication that can or should be administered when the then-existing health parameters of the patient dictate.

In this arrangement, the control element includes internal memory for storing the prescribed schedule for administering medication. The control element also includes external input apparatus for receiving and interpreting information indicative of selected one or more health parameters of the patient. In this arrangement, the first delivery mechanism is actuated in response to the prescribed schedule, but not in response to the receipt of information by the external input apparatus. On the other hand, the control element will actuate the second delivery mechanism in response to the receipt and interpretation of health parameter information by the external input apparatus.

In one embodiment of this arrangement, the device includes an external output for prompting preselected information of a qualitative nature from the patient. The device also includes an input for receiving and interpreting responses made by the patient to the prompting of the external output. The associated external input apparatus includes testing apparatus for the patient to quantitatively measure a preselected physical parameter. The control element correlates the quantitative measurement by the testing apparatus with the qualitative responses received and generates a control signal to actuate the second delivery mechanism when a predetermined correlation is found to exist.

In a preferred embodiment of the invention, the control element includes a timer for preventing a second actuation of the second delivery mechanism, despite the receipt of an otherwise proper actuating command, when the time period between a first and second actuation is less than a prescribed period. The risk of mismedication of on demand-type medication is thereby minimized.

Also in a preferred embodiment, the external input includes a speech recognition device for receiving and interpreting at least one prescribed verbal command made by the patient. In this arrangement, the device also preferably includes a speech output apparatus for generating audible messages to the patient. The personal, interactive nature of the device is thereby enhanced.

In accordance with the invention, the device may also include a mechanism for altering a prescribed medication schedule in response to the receipt of a prescribed change schedule command from the physician or user.

In another aspect, the invention further provides a system that operates in response to the command signals generated by the control element for maintaining a data file for each medication dispensing device. The data file includes one or more records reflecting information of use for inventory control and management purposes.

The invention provides a device that can oversee and administer a relatively complex regime of different types of medication in a flexible and user-friendly manner. By integrating relatively unyielding compliance to a prescribed schedule for certain medication with an accommodating approach to other types of medication, the invention provides the patient with an automated caregiver that is strict in certain respects but responsive in others.

Other features and advantages of the invention will become apparent upon reviewing the following detailed description, drawings, and appended claims.

BRIEF DESCRIPTION OF THE DRAWINGS

FIG. 1 is a front perspective view of a patient monitoring and assistance device having an enclosed system for delivering physical testing devices to the patient, as well as an enclosed medication storage and dispensing system that embodies the features of the invention for storing and dispensing medication in individual caplets, each of which systems is shown in its closed position;

FIG. 2 is a front perspective view of the device shown in FIG. 1, with the testing device delivery system and medication delivery system each shown in its open position;

FIG. 3 is an enlarged perspective view, with portions broken away, of the interior of the device shown in FIG. 2, showing the enclosed medication storage and dispensing system;

FIG. 10 is an enlarged side view, partially broken away, of the medication delivery system shown in FIG. 3, tipped outwardly from the rear of the associated patient assist device for replenishment of medication;

FIG. 11 is an enlarged side view, partially broken away, of the medication delivery system shown in FIG.

Figure 15:
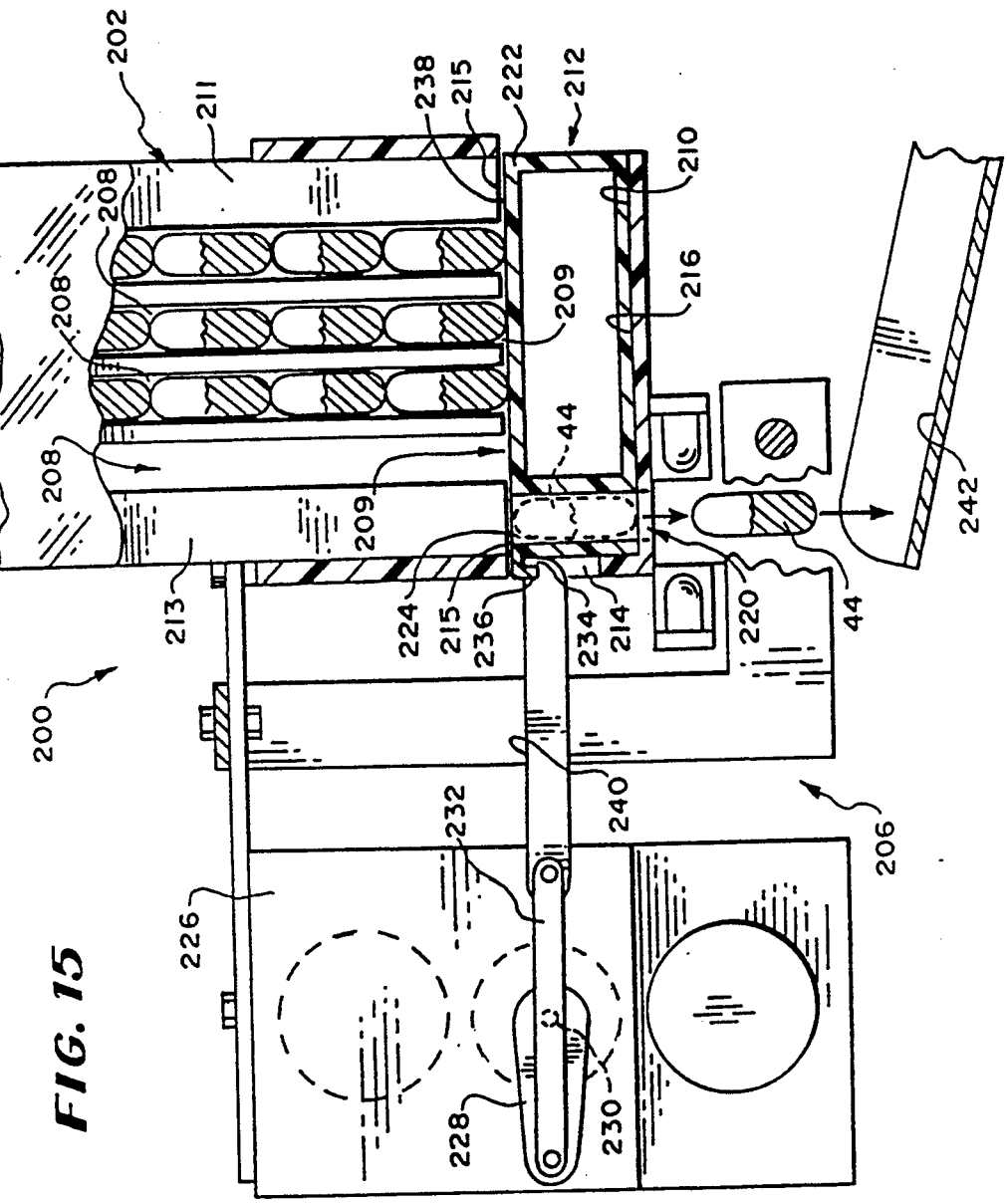
Figure 16:
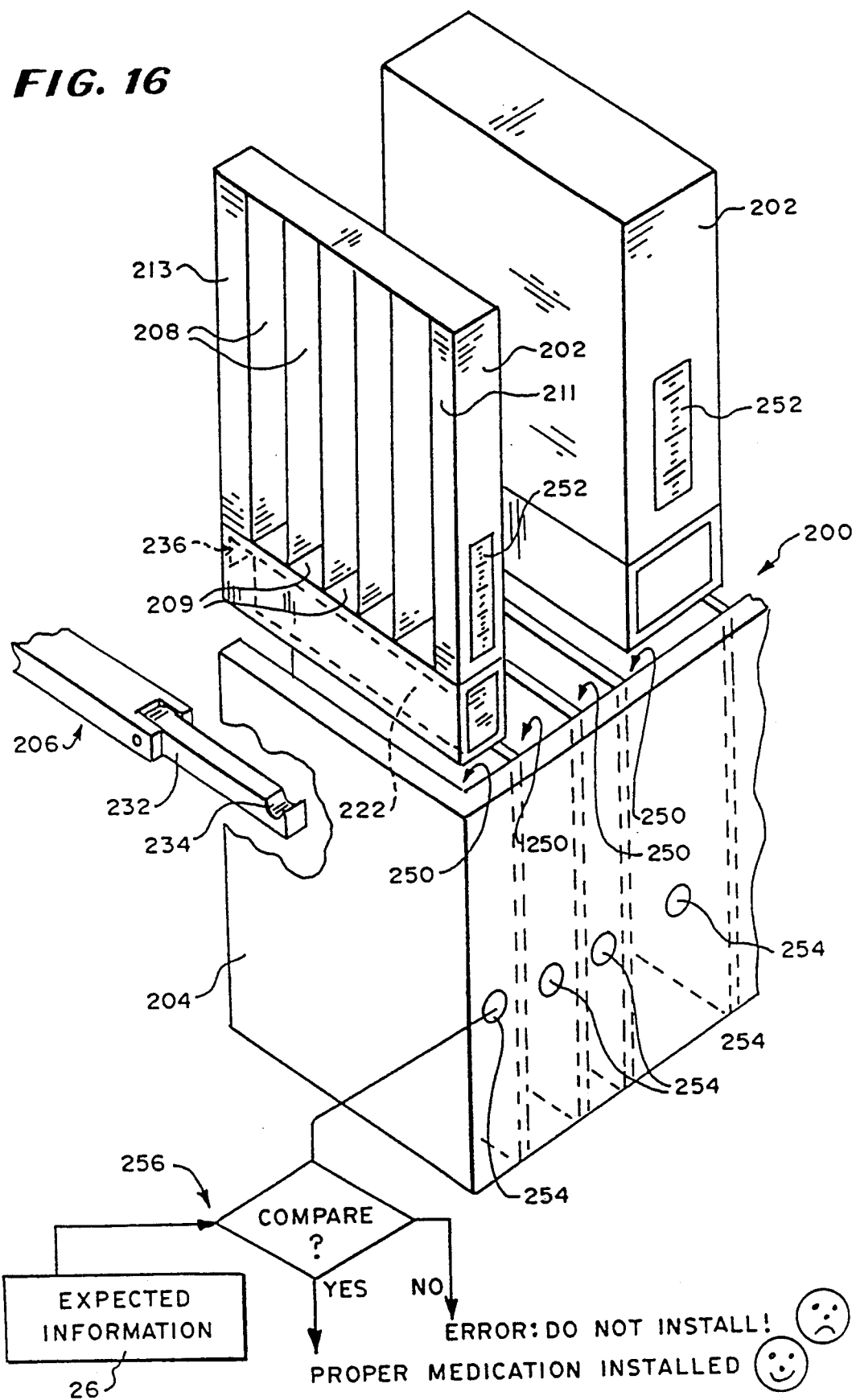
Figure 17:
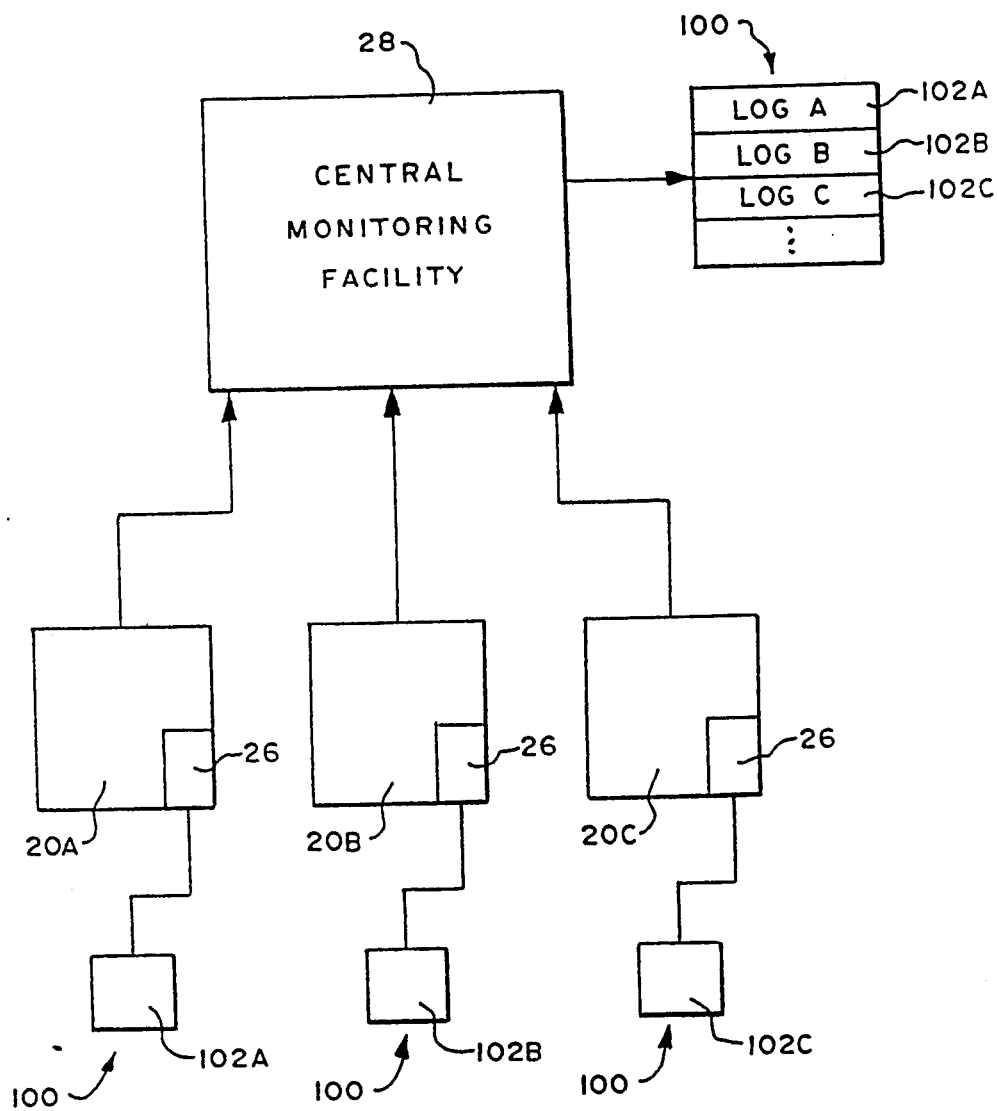
Figure 18:
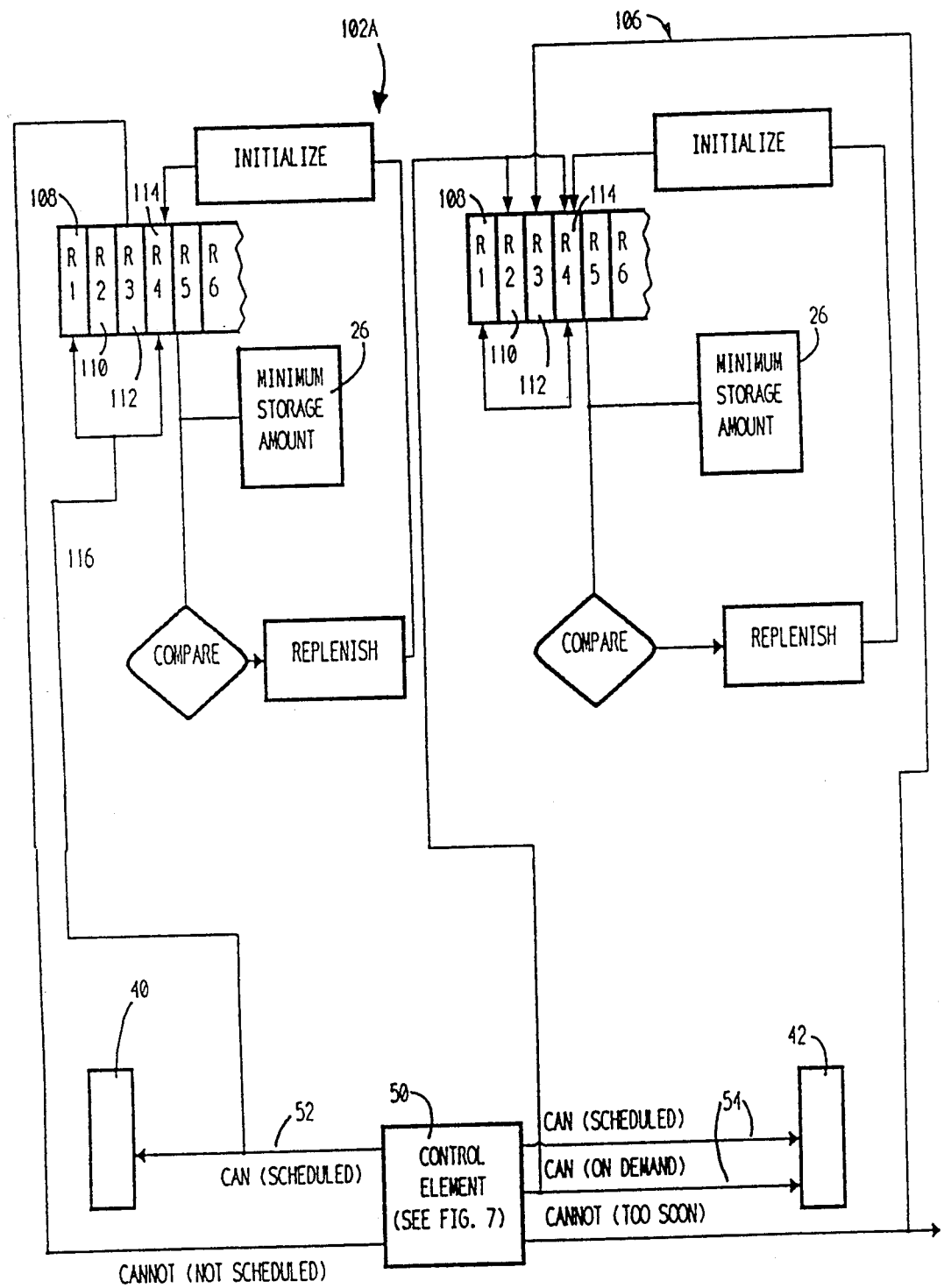
Figure 19:
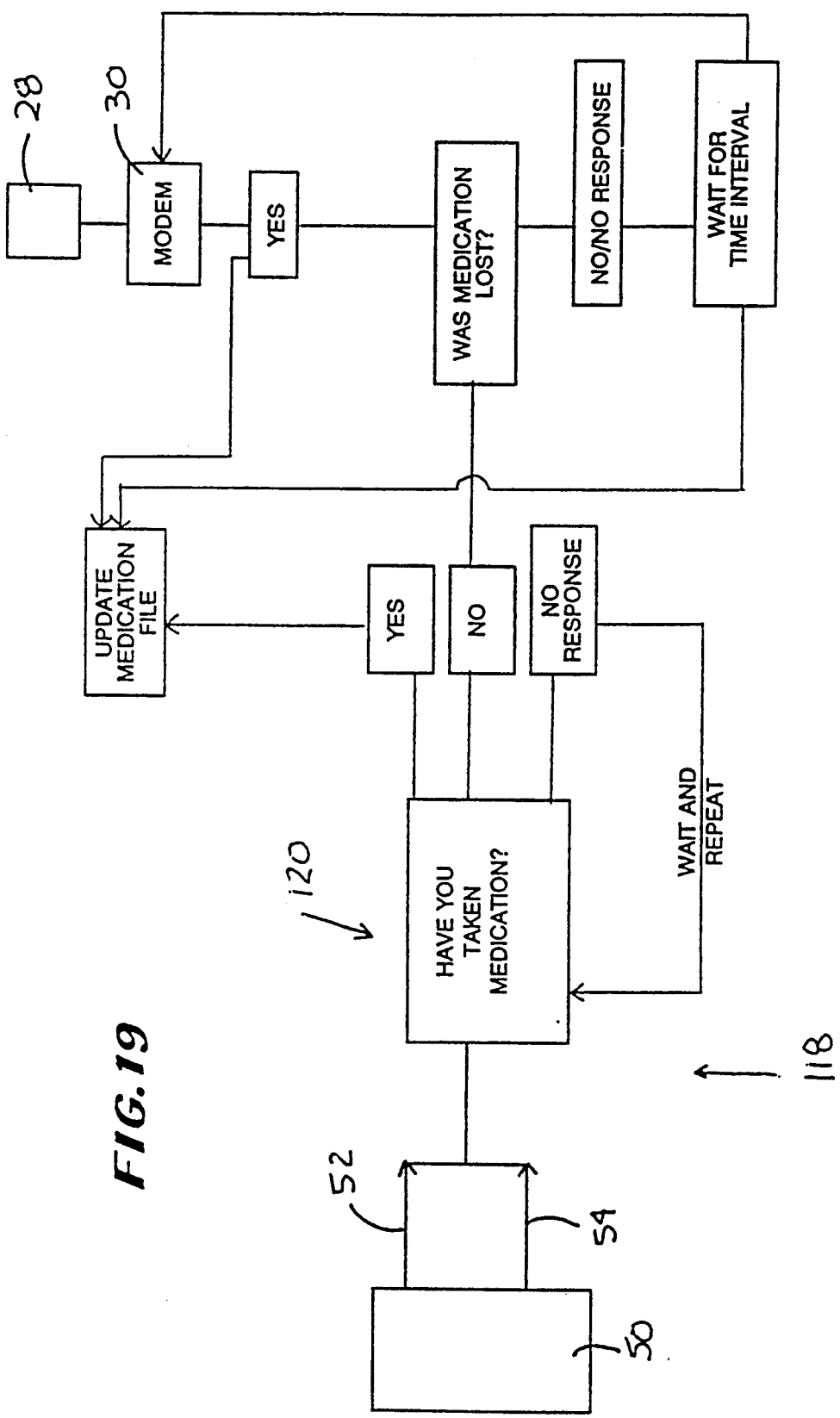

3 in its operative position within the associated patient assist device;

FIGS. 12 to 15 are enlarged side views of the medication delivery system taken generally along line 12—12 in FIG. 3, showing the sequence of operation in dispensing medication in caplet form;

FIG. 16 is a perspective view of the medication delivery system shown in FIG. 3 as it is being replenished;

FIG. 17 is a schematic and partially diagrammatic view of a medication inventory and management system that embodies the features of the invention;

FIG. 18 is a schematic and partially diagrammatic view of medication files contained in the inventory and management system shown in FIG. 15; and FIG. 19 is a schematic and partially diagrammatic flow chart of a medication administration follow up sequence that forms a part of the inventory and management system shown in FIG. 15

DESCRIPTION OF THE PREFERRED EMBODIMENTS

One preferred embodiment of an interactive monitoring and assistance device 10 is shown in FIGS. 1 and 2. As will soon be described in greater detail, the device 10 performs as a self-contained, microprocessor-based caregiver who, in a friendly and supportive manner, monitors, manages and assists a patient in performing everyday health maintenance tasks. In carrying out its tasks, the device 10 monitors the patient's vital signs. The device 10 also stores and administers medication. The device 10 preferably is linked to a central facility that provides round-the-clock supervision and response as required.

The device 10 includes a housing or cabinet 12 that, in a preferred design, stands about four feet tall. Preferably, the housing 12 is portable. For this purpose, the device 10 includes wheels 14 and a handle 16 for the patient, or another user, to guide the movement.

As shown in FIGS. 1 and 2, the device 10 houses a system 18 for storing and delivering one or more devices for testing the vital signals of a patient. The device 10 also houses a system 20 for storing and administering medication (see FIG. 3 also).

Figure 4A:
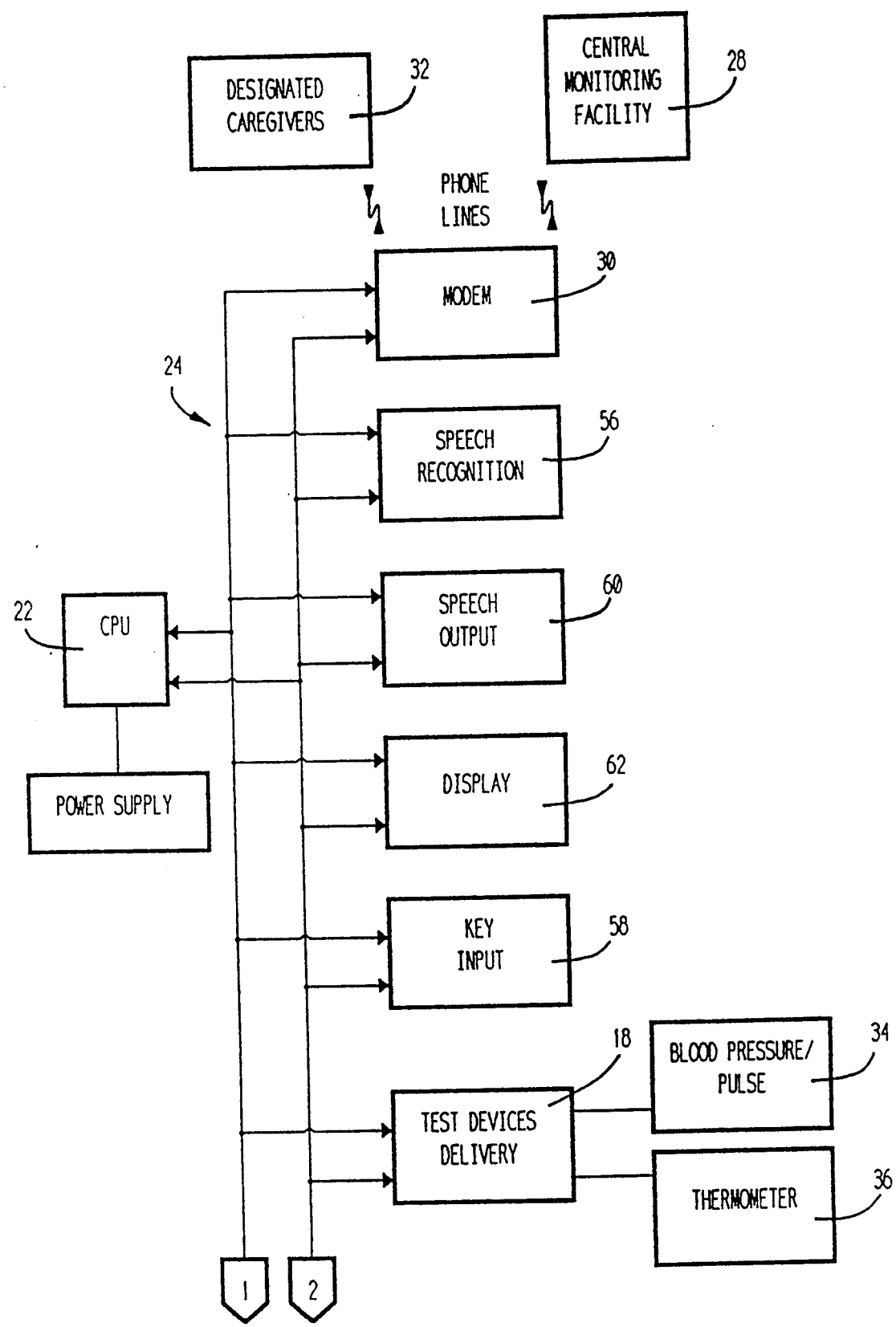
FIGS. 4a and 4b, collectively referred to hereinafter as FIG. 4, are a schematic block diagram of the system that controls the operation of the patient assist device shown in FIG. 1.
Figure 4B:
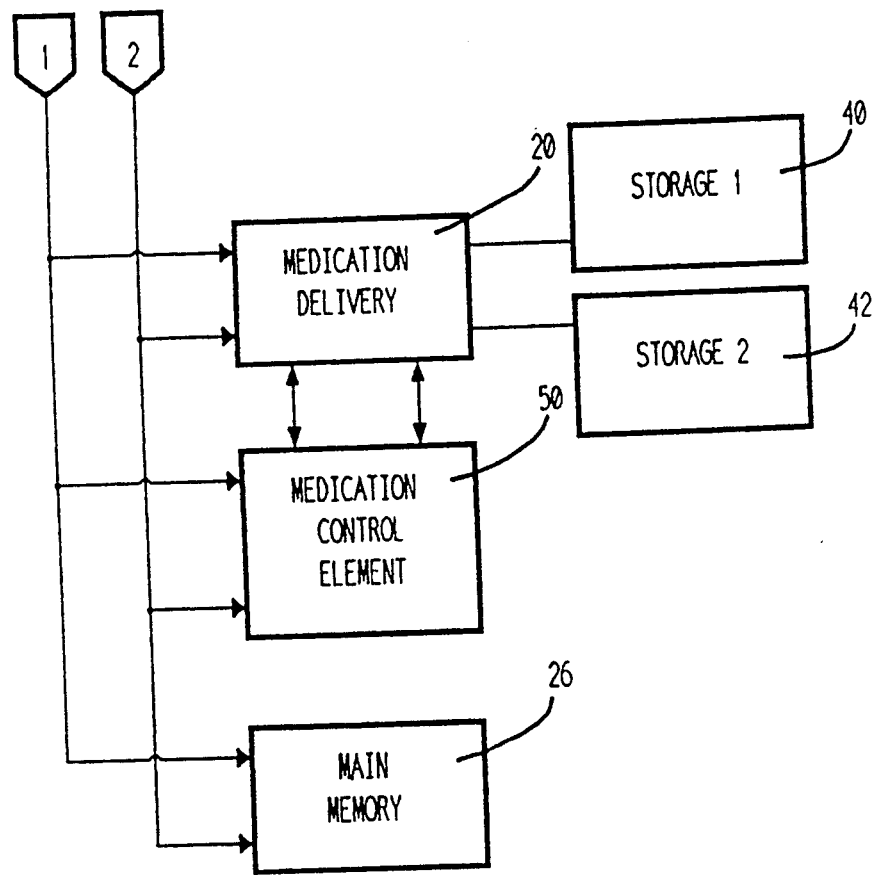

In the illustrated and preferred embodiment shown in FIG. 4, the device 10 houses a main microprocessor-based CPU 22 that coordinates and controls its operation. While various arrangements are possible, the CPU 22 preferably comprises an IBM PC compatible CPU board that accommodates multi-tasking sequences. Various input/output (I/0) devices communicate with the main CPU 22 through conventional data and address busses 24. The I/0 devices will be described in greater detail later. A mass storage device 26 for storing digital information also communicates with the main CPU 22 through the busses 24.

In use, as shown in FIG. 4, the device 10 is preferably linked with a central monitoring facility 28 by a modem 30 that communicates with the main CPU 22 through the busses 24. Health care professionals are present on a twenty-four hour basis at the central facility 28 to monitor the health of the patient based upon information collected and transmitted to them by the device 10. The device 10 is also preferably linked via the modem 30 with selected individuals 32—typically close friends, family members, or other designated caregivers—who are automatically notified by the device 10 when certain health conditions exist or upon request by the patient or central facility 28. As can be seen, the device 10 is a central part of an overall support system for the patient.

As shown in FIG. 2, the system 18 for monitoring the patient's vital signs includes two physical testing devices: a pressure cuff 34 for measuring blood pressure and pulse rate, and a thermometer 36 for measuring body temperature. Of course, other testing devices could be provided, depending upon the health condition of the patient and mode of treatment. As used in this Specification, the term "physical test" broadly includes tests of body functions (pulse, respiration, temperature, etc.) and tests of body fluids (blood, urine, saliva, etc.) by noninvasive and invasive techniques, including ultrasonic and radiographic methods.

As shown in FIG. 4, the testing devices 34 and 36 communicate with the main CPU 22 through the busses 24. The measurements taken are stored in the data storage device 26. These measurements are also periodically transmitted to the central monitoring facility 28 by the modem 30. The central facility 28 also preferably records received information in its own mass storage device for record keeping, retrieval and analysis.

Preferably, the testing devices 34 and 36 are housed in a movable compartment or drawer 38 within the housing 12. The drawer 38 is normally closed (as shown in FIG. 1), thereby retaining the testing devices 34 and 36 within the housing 12 away from access by the patient. The drawer 38 will open in response to an appropriate command signal received and interpreted by the main CPU 22. The opened position for the drawer 38 is shown in FIG. 2. The testing devices 34 and 36 are thereby made available for use by the patient. This particular operation will be described in greater detail later.

The medication delivery system 20 housed within the device 10 (see FIG. 3) embodies the features of the invention. The system 20 is capable of storing and administering different types of medications having different administration criteria. The criteria can differ in terms of prescribed dosage amount, prescribed frequency of administration, degree of accessibility to the patient, or various combinations of the above.

The medication delivery system 20 includes at least two discrete storage compartments or cassettes (generally designated 40 and 42 in FIG. 3) within the housing 12. Each storage compartment 40 and 42 is separate and self-contained. Each compartment 40 and 42 is capable of independently storing at least one dose of a medication 44 within the housing 12 away from access by the user.

The medication delivery system 20 further includes independent delivery means or mechanisms associated with each storage compartment 40 and 42. In the illustrated arrangement (see FIGS. 3 and 5), a first delivery mechanism 46 is associated with the first storage compartment 40 for selectively delivering a medication dose from there to the patient. A second delivery mechanism 48 is likewise associated with the second storage compartment 42 for selectively delivering a medication dose from there to patient.

The number of individual delivery systems provided corresponds with the number of individual medication storage compartments. The number of storage compartments can, of course, vary. Only two storage compartments and their associated delivery systems will be discussed.

The first and second delivery mechanisms 46 and 48 operate independently and in response to different administration criteria. For this purpose (in particular, see FIG. 5), the medication delivery system 20 includes a control means or element 50 associated with the first and second delivery mechanisms 46 and 48. In the illustrated and preferred embodiment, the control element 50 communicates with the main CPU 22 (see FIG. 4, too), either in the form of programmable random access memory (RAM) or as preprogrammed read only memory (ROM).

According to its programming, the control element 50 is capable of receiving and differentiating between at least two different prescribed inputs. Upon the receipt and interpretation a first prescribed input or combination of inputs, the control element 50 will generate a control signal 52 that actuates the first delivery mechanism 46. Upon receipt of the second prescribed input or combination of inputs different from the first input, the control element 50 will generate a control signal 54 that actuates the second delivery mechanism 48. The control element 50 will not actuate the first delivery mechanism 46 in response to the second prescribed input.

Because the first and second control signals 52 and 54 are generated in response to different prescribed input criteria, the medications stored in the two storage compartments 40 and 42 can be selectively administered differently.

Figure 5:
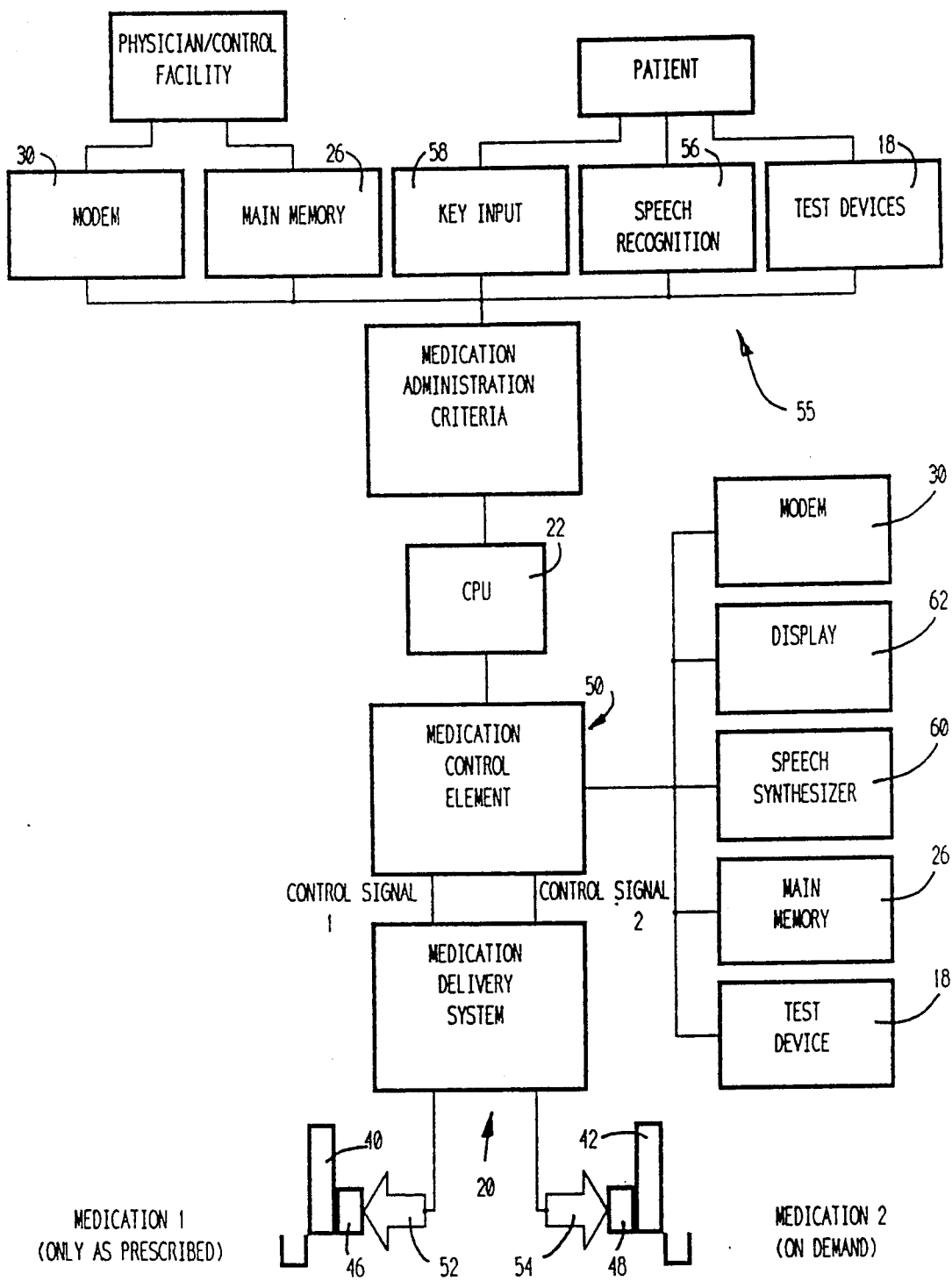
FIG. 5 is a schematic and partially diagrammatic block diagram of the elements of the system shown in FIG. 4 that control the operation of the medication delivery system that incorporates the invention.

As best shown in FIG. 5, the input criteria that generate the first and second control signals are derived from both external and internal devices 55 associated with the medication delivery system 20. These devices receive input from internal memory 26, the physician (or healthcare professional), and the individual patient.

More particularly, the system 20 includes in internal memory 26 one or more prescribed schedules for administering medication. Here, the attending physician records the medication regime he or she has prescribed for the patient.

The system 20 also includes various external input devices for receiving and interpreting prescribed commands either from the patient or from the central monitoring facility 28. These external input devices communicate with the control element 50 through the main CPU 22 (see FIG. 4). The received commands can include one or more specified commands for administering medication "upon demand".

In the illustrated and preferred embodiment shown in FIGS. 4 and 5, the external input devices include a speech recognition system 56 for receiving and interpreting preselected verbal commands made by the patient (for example, by using a Texas Instruments Recognition and Speech Unit Model TI-2245186-001). The external input devices also include the modem 30 for receiving and interpreting preselected commands from the central facility 28.

In addition, the external input devices preferably include one or more input buttons or keys 58 located at a user-convenient place on the housing 12. The keys 58 allow the patient to manually enter the prescribed medication delivery commands, if desired. In the illustrated and preferred embodiment shown in FIGS. 1 and 2, only a select few input keys 58 for entering block (or macro-) commands are provided. This arrangement simplifies the patient's interface with the device 10. However, it should be appreciated that a full keyboard could also be included, depending upon the degree of sophistication and desires of the patient.

In the illustrated and preferred embodiment shown in FIGS. 4 and 5, the system also includes an external output device associated with the main CPU 22 for delivering messages or otherwise communicating with the patient. Preferably, the external output device includes a speech generation system 60 for generating audible messages to the user. The speech generation system 60 can take the form of either a conventional device that synthesizes speech or a conventional device that digitizes prerecorded speech.

In addition, the external output device also preferably includes a video monitor 62 on which the audible messages appear in written form (see FIGS. 1 and 2 also). In this arrangement, the video monitor 62 can also display in written form the preselected medication administration commands. In this way, the video monitor 62 serves to visually back up and confirm the verbal messages and commands being exchanged by the patient and the device 10, thereby minimizing the chance of misunderstandings or failures to communicate.

Due to these various input and output devices, the medication delivery system 20 as just described affirmatively interacts with the patient, relying upon both spoken and written forms of communication with the patient.

System for Storing and Administering Scheduled Medication and On Demand Medication In accordance with one aspect of the invention, the control element 50 as above described can store and selectively administer one category of medication that should be administered only according to a prescribed schedule and another category of medication that can be administered upon demand by the patient.

Figure 6A:
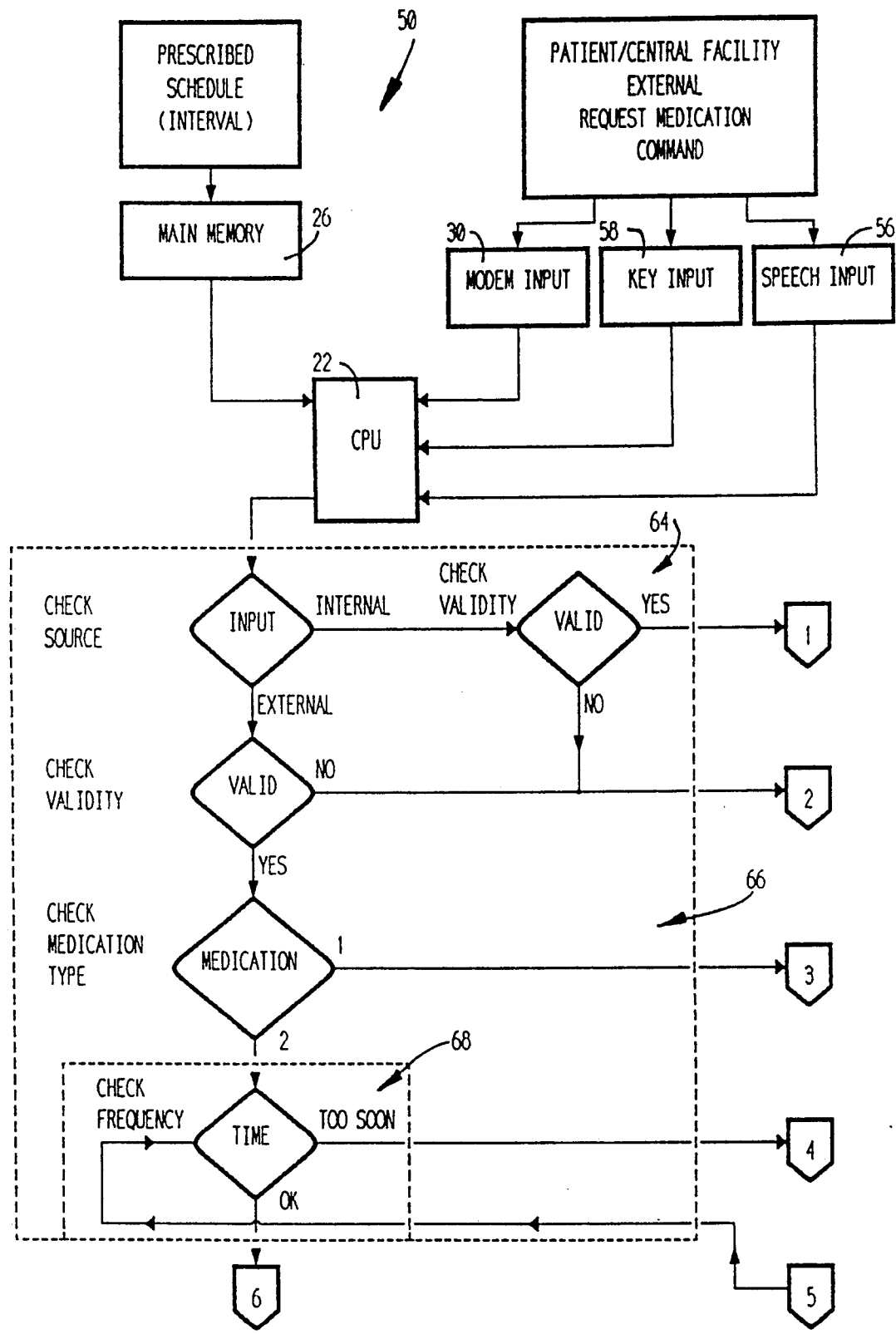
FIGS. 6a, 6b, 7a, 7b, 8a, 8b, 8c, 9a, and 9b are schematic and partially diagrammatic flow charts of differing embodiments of the system for controlling the operation of the medication delivery system that incorporate aspects of the invention.
Figure 6B:
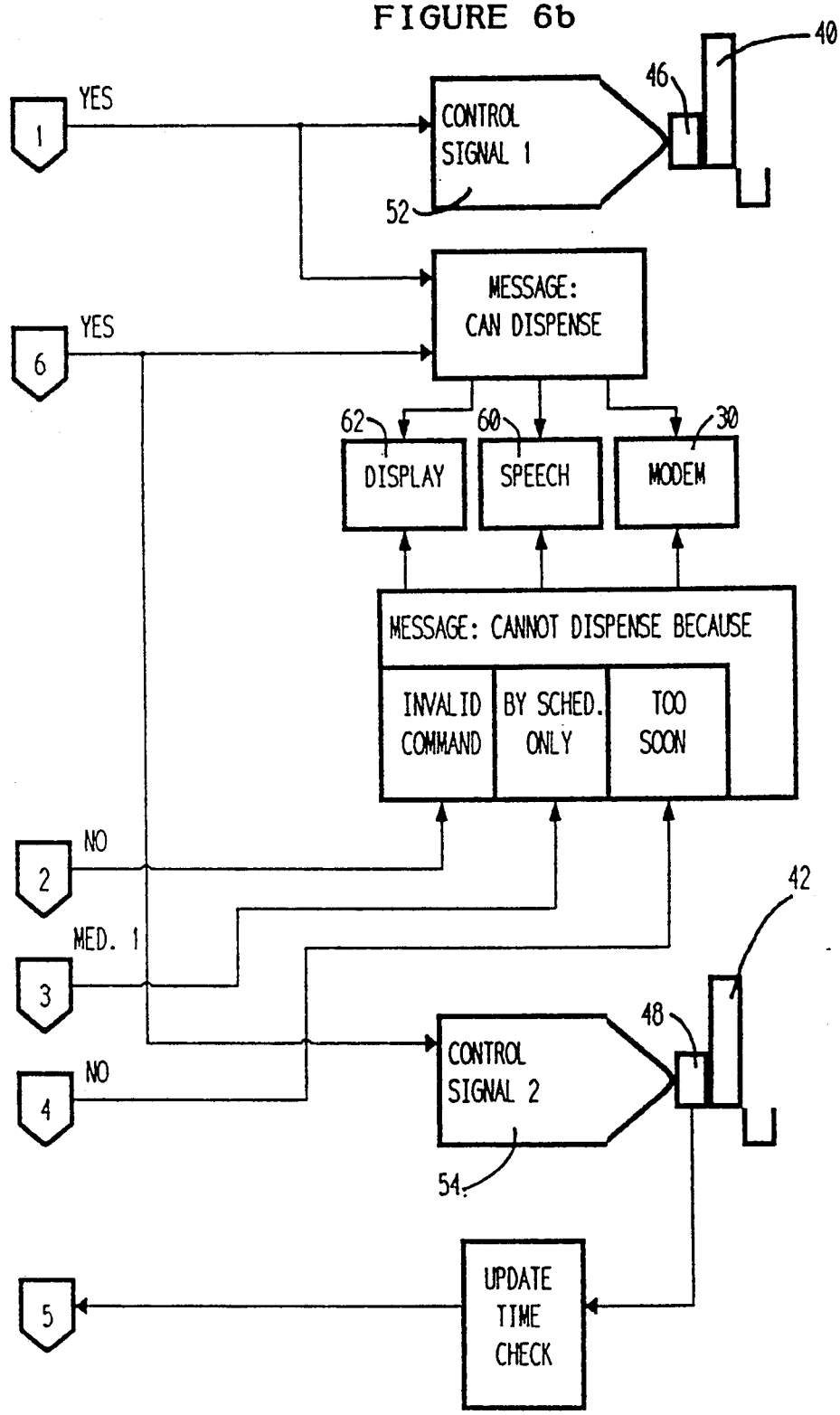

The control element 50 associated with this arrangement is shown diagrammatically in FIG. 6. The prescribed medication schedule is retained in the internal memory 26. The control element 50 includes a first operative sequence 64 that will generate the first control signal 52 upon receiving a valid administer medication command from an internal source (that is, a command generated internally based upon preprogrammed considerations). In the illustrated embodiment, the appropriate administer medication command is internally issued periodically by the CPU 22, based upon a continuous real time monitoring of the prescribed medication schedule stored in the internal memory 26.

Upon generation of the first control signal 52, medication retained in the first storage compartment 40, and only the first storage compartment 40, will be released to the patient.

Preferably, the first operative sequence 64 also generates a "Can Administer" message, using one or more of the output devices (the speech generator 60 and/or the display 62), advising the patient that the prescribed medication is being dispensed according to schedule.

The control element 50 also includes a second operative sequence 66 that, in association with the external input devices (modem 30/key input 58/speech recognition 56), receives and interprets one or more medication delivery commands received from an external source, such as the patient or the central facility 28. As shown in FIG. 6, the second operative sequence 66 conducts a validity check upon the command. The second operative sequence 66 also checks to determine what type or category of medication is being requested.

Upon receipt of a valid command or commands requesting the proper type of medication, the second operative sequence 66 generates the second control signal 54. The medication retained in the second storage compartment 42, but not the first storage compartment 40, is thereby released to the patient.

The second operative sequence 66 also preferably communicates an appropriate "Can Administer" message to the patient through one or more of the output devices 60/62. If the medication request originates from the patient, an advisory message may also be sent to the central facility 28 via the modem 30 at the time an "on demand" request is received and implemented.

If an invalid command is received, or if the patient requests a medication that can only be administered according to an internal command from the internal memory, an appropriate "Cannot Dispense" message is display and/or spoken using the output devices 60/62.

Preferably, whenever a decision is made to either dispense medication or withhold medication, the decision is recorded in internal memory 26 for record keeping purposes.

The first delivery mechanism 46 is thereby actuated in response to an internally generated command signal, but not in response to an externally generated command signal. The first category of medication can thus be safely retained within the first storage compartment 40 away from patient access, except as controlled by the control element 50 (via the first control signal 52). Strict compliance with the prescribed medication schedule is assured.

The second delivery mechanism 48 is actuated in response to the second control signal 54 based upon externally received commands. The second category of "on demand" medication can thus be safely retained in the second storage compartment 42 for administration externally controlled by the patient or the central facility 28 by issuing a proper external command.

In the illustrated and preferred embodiment shown in FIG. 6, the control element 50 also includes a third operative sequence 68 that maintains a real time record of "on demand" administrations of medication and the elapsed time period between them. The third operative sequence 68 includes timing means 70 for comparing the elapsed time between one actuation and the next subsequent actuation command to a prescribed fixed interval. The third operative sequence 68 will, based upon the output of the timing means 70, prevent the next subsequent actuation of the second delivery mechanism 48, despite the receipt of a valid medication command, when the elapsed time period is less than the prescribed period.

In the illustrated and preferred embodiment, the third operative sequence 68 also informs the patient through an appropriate "Cannot Administer" message via one or more of the output devices 60/62. In addition, an advisory message can also be transmitted to the central facility 28 via the modem 30. In this way, the system guards against mismedication or overuse of the "on demand" category of medication.

In accordance with another aspect of the invention, the medication delivery system is also adaptable to a situation in which a first category of medication is to be administered only in accordance with a prescribed schedule, while the second category of medication is also administered periodically in accordance with the same or different prescribed schedule, but can also be administered on demand. The control element 50 of this arrangement is shown diagrammatically in FIG. 7. Components shared with the control element 50 shown in FIG. 6 are given the same reference numerals.

In this arrangement, the second operative sequence 66 actuates the second delivery mechanism 42 in response to either a valid internal signal from the prescribed schedule stored in the internal memory 26 (received via preferred path 72 or alternate path 72A in FIG. 7), or in response to the receipt of a valid prescribed medication delivery command from one of the external input devices 30/56/58, as before described. Again, timing means 70 is preferably provided (with preferred path 72) to assure that mismedication or overuse does not occur. The prescribed schedule for the second category of medication can be the same as for the first category. Or, as shown in FIG. 7, the different categories of medication have different prescribed schedules.

As before, the second operative sequence 66 also preferably advises the patient, through one or more of the output devices 60/62, upon the release of or the refusal to release the requested medication.

System for Storing and Administering Medications According to Different Schedules As just briefly discussed, in another aspect of the invention, the control element 50 is also applicable for use when medication is to be administered according to different prescribed schedules. The control element 50 of this arrangement is also shown diagrammatically in FIG. 7.

Figure 7A:
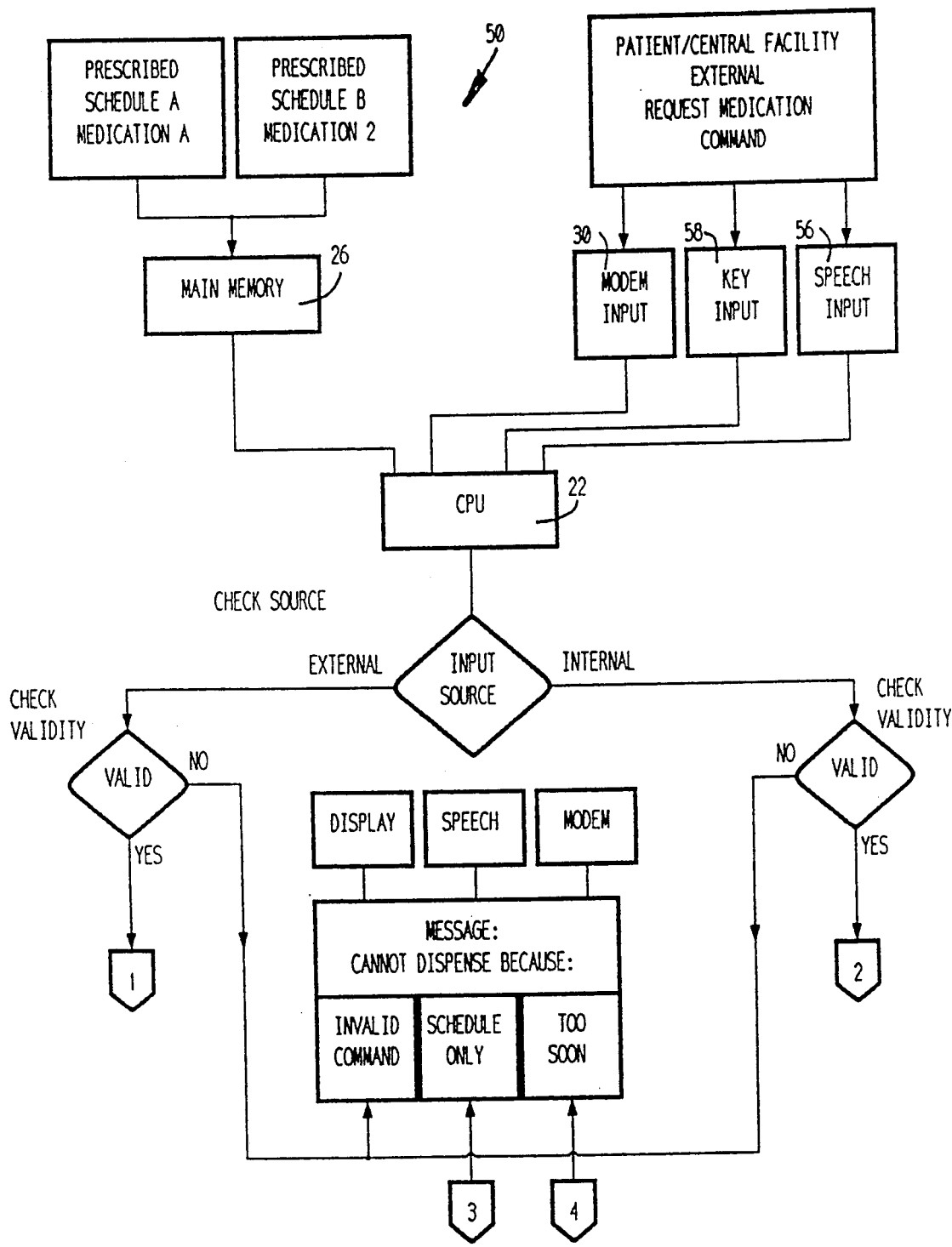
Figure 7B:
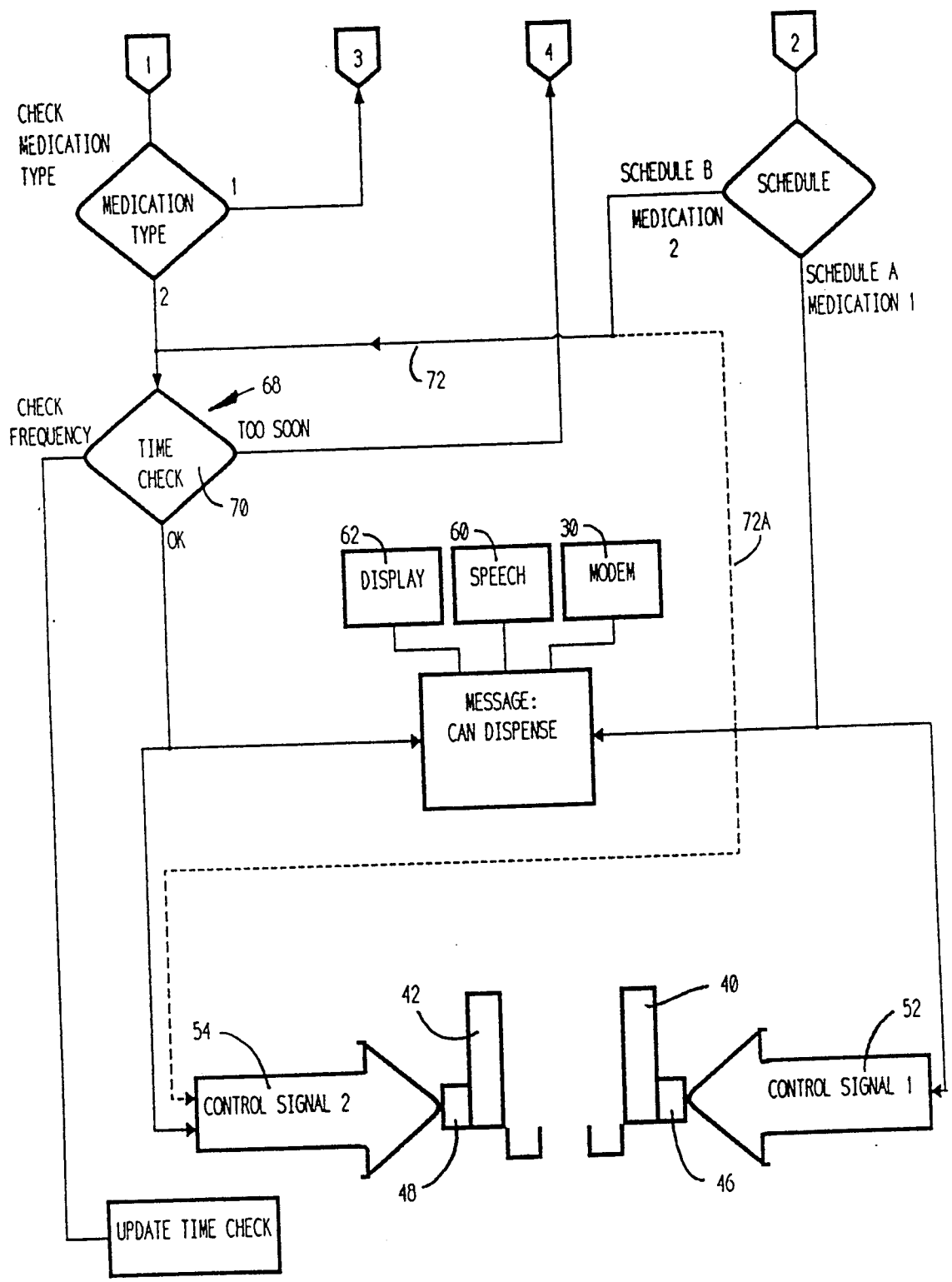

In this arrangement, the first and second prescribed medication administration schedules are separately stored in the memory device 26 (designated Schedule A and Schedule B in FIG. 7). The first operative sequence 64 of the control element 50 generates the control signal 52 to actuate the first delivery mechanism 46 in response to a valid signal based upon the first prescribed schedule (Schedule A), but not in response to the second prescribed schedule (Schedule B). The second operative sequence 66 responds to a valid signal based upon the second prescribed schedule (Schedule B) to generate the control signal 54 actuating the second delivery mechanism 48.

System for Storing and Administering Medication According to Present Health Parameters In accordance with yet another aspect of the invention, the control element 50 is also applicable for use when the different input criteria discriminate between one category of medication that can be administered only according to the schedule prescribed by the physician and another category of medication that can or should be administered when the then-existing health parameters of the patient dictate. The control element 50 of this arrangement is shown diagrammatically in FIG. 8. Components shared with the control elements 50 shown in FIGS. 6 and 7 are again given the same reference numerals.

In this arrangement, like the arrangements previously described, the prescribed schedule for administering medication is stored in the memory device 26. The first operative sequence 64 responds to this schedule in generating the first control signal 52, as previously described and shown in FIG. 6.

Figure 8A:
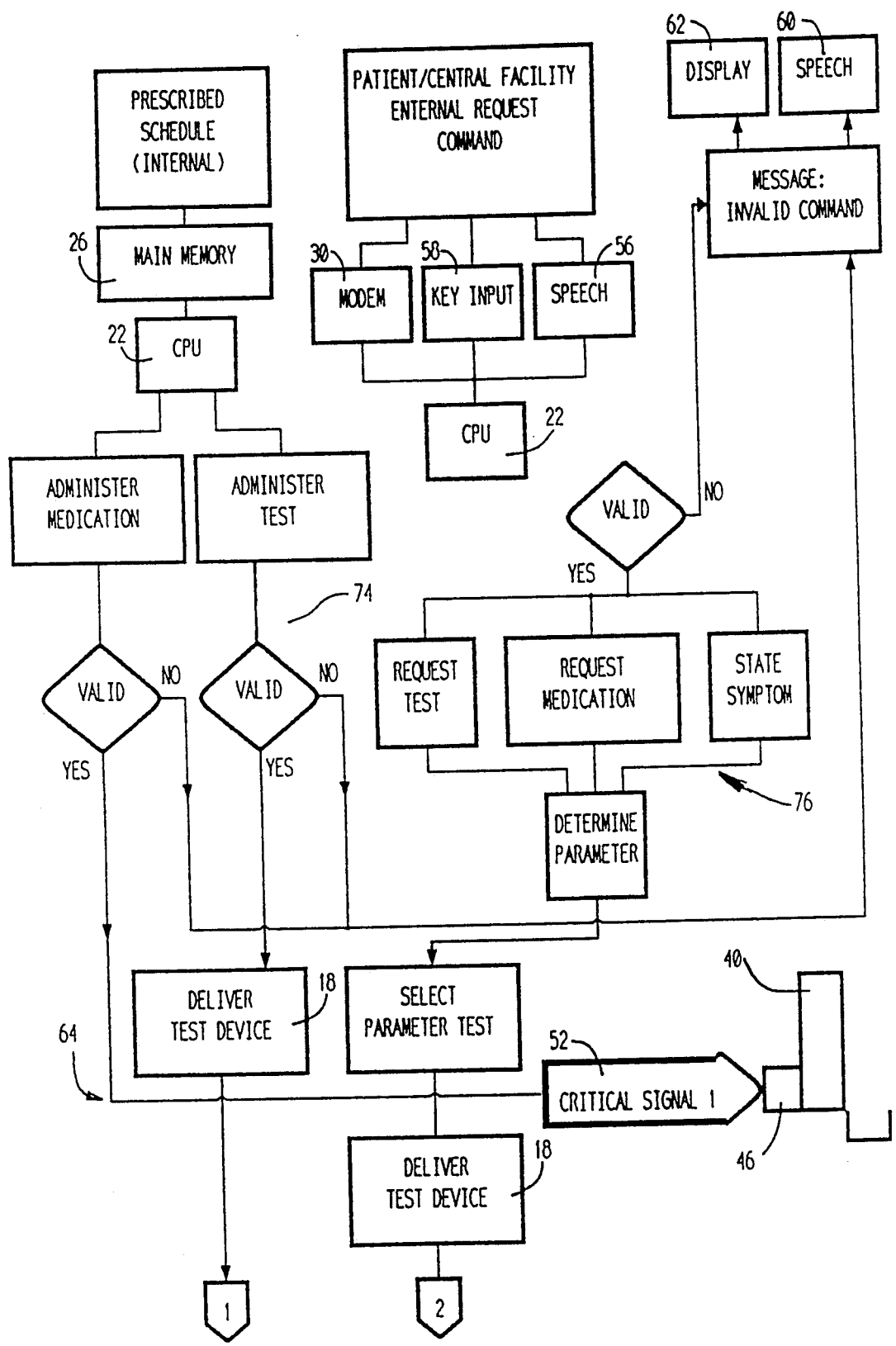
Figure 8B:
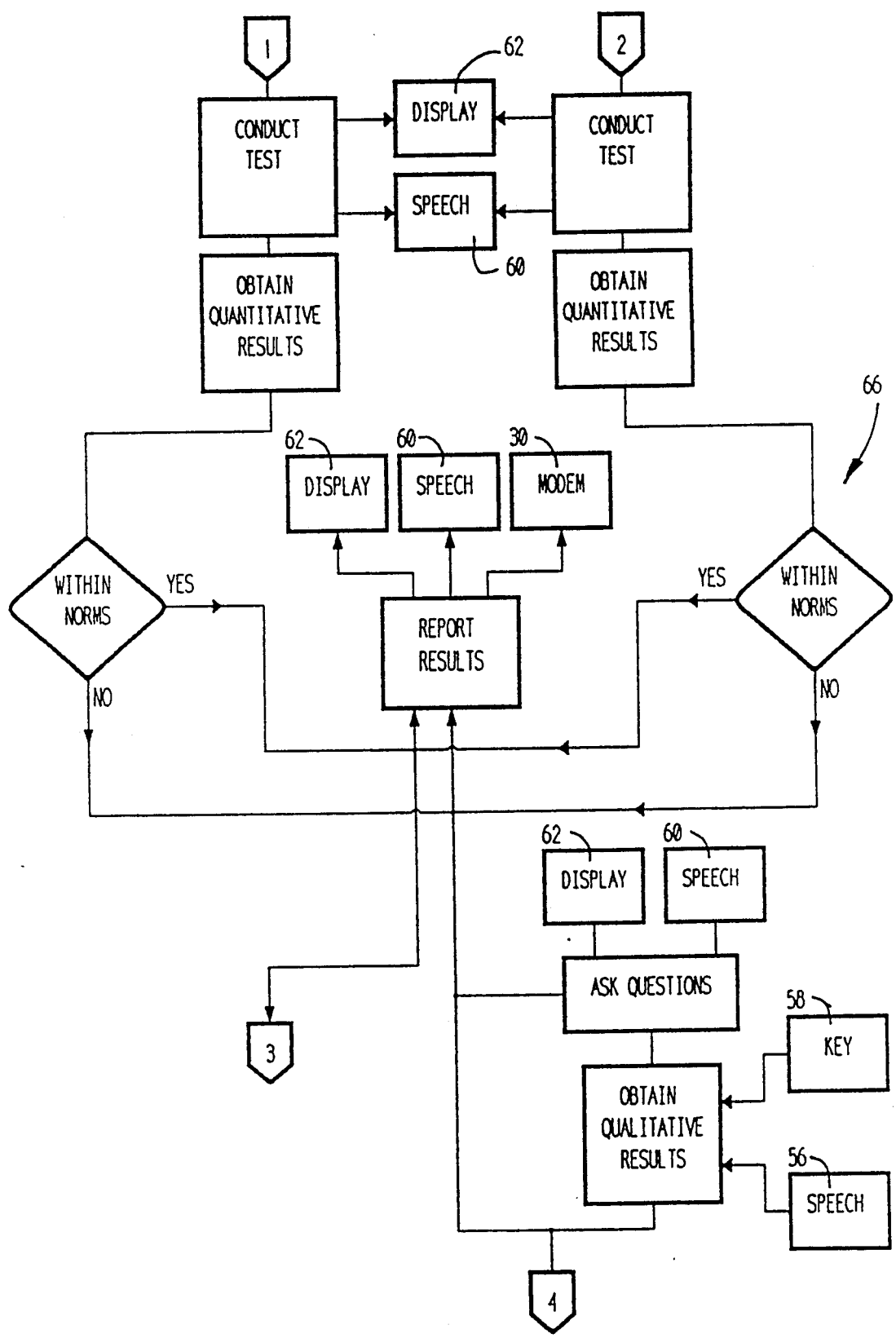
Figure 8C:
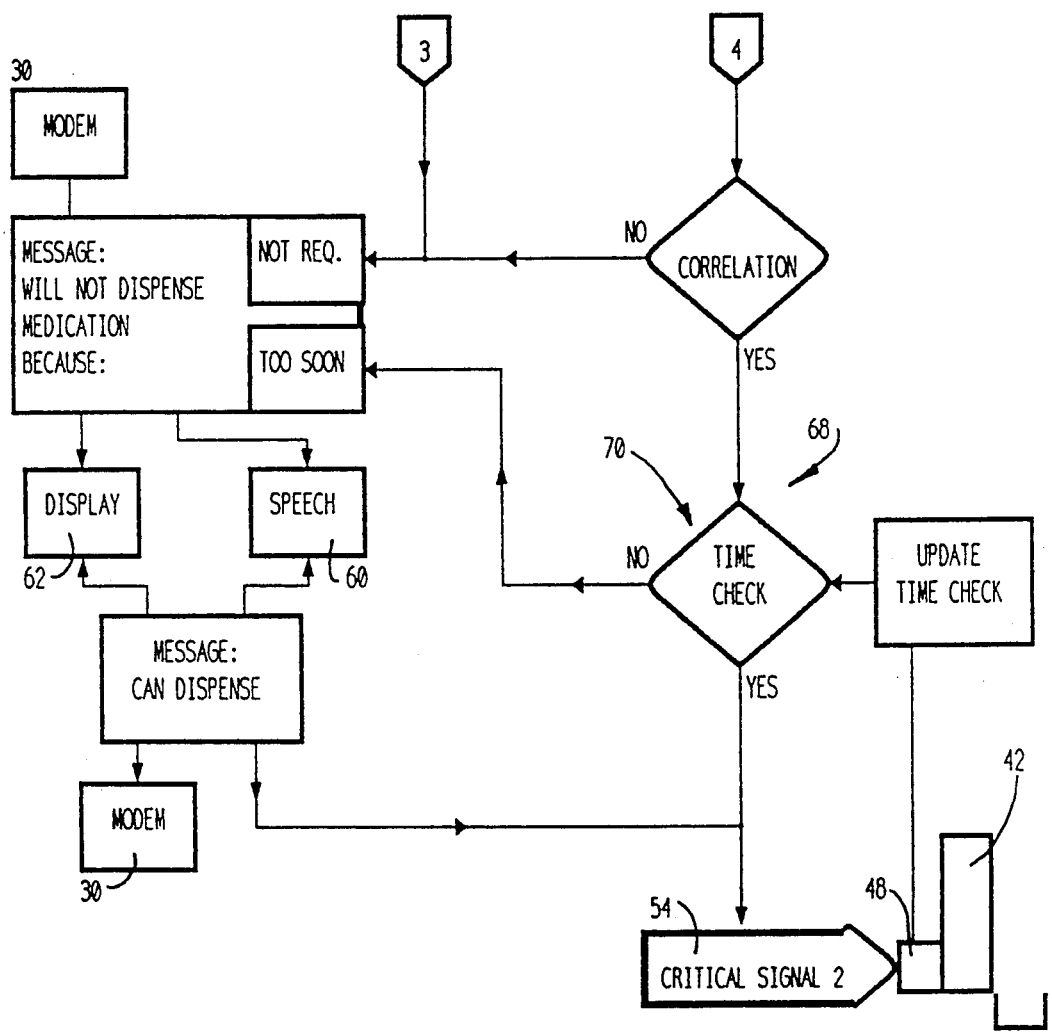

Unlike the other arrangements, however, the second operative sequence 66 shown in FIG. 8 receives and interprets information indicative of selected one or more health parameters of the patient. The second operative sequence 66 compares and correlates this information. If a prescribed correlation exists, indicating an abnormal health parameter that may respond to medication, the second operative sequence 66 generates the second control signal 54 to administer the appropriate medication through the second delivery mechanism 48.

In the illustrated and preferred arrangement shown in FIG. 8, the second operative sequence 66 collects its information from several different sources. One input comprises the quantitative measurements derived from the physical testing system 18. Another input comprises qualitative information received from the patient through the external input devices 56/58. Preferably, the second operative sequence 66 affirmatively interacts by prompting the patient, using the external output devices 60/62, to provide the qualitative and quantitative information necessary for the second operative sequence 66 to perform its required comparison and correlation sequence.

In the illustrated and preferred arrangement shown in FIG. 8, the second operative sequence 66 itself is prompted into action in one of two ways. In one sequence (path 74 in FIG. 8), an "Administer Test" signal is automatically generated according to a prescribed schedule stored in the main memory 26. This schedule carries out the attending physician's orders to periodically check the vital signs of the patient.

In another sequence (paths 76 in FIG. 8), the "Administer Test" signal is generated in response to an external command issued by the patient or by the central facility 28. For example, the patient can issue a prescribed command by voice (through input 56) or by key input 58 indicating a particular physical symptom ("I feel like I have a fever"), or a generalized feeling of discomfort ("I don't feel good"). Alternatively, the patient can issue a prescribed command requesting a specific test ("Check my temperature") or request medication ("Give me my pain pills").

The second operative sequence 66 preferably responds initially by requiring further information from the patient through a predetermined sequence of questions designed to isolate the particular physical parameter of concern. These requests are communicated through the output devices 60/62, and the responses are received through the input devices 56/58. Once the source of the physical problem is determined, the proper "Administer Test" signal is generated.

However generated, the "Administer Test" signal opens the drawer 38 (as shown in FIG. 2) to make the proper testing device(s) 34/36 available for use by the patient. The "Administer Test" signal also prompts the patient through the output communication devices 60/62 to conduct the desired test or tests.

In the illustrated embodiment (see FIGS. 10 and 11), the drawer 38 is biased toward an opened position by a control spring 76 (as shown in FIG. 10). A solenoid controlled locking mechanism 78 normally retains the drawer 38 in the closed and locked position (as shown in FIG. 11). An "Open" signal to the solenoid releases the locking mechanism 78 to allow the drawer 38 to open in response to the control spring 76. Other mechanisms can be used to accomplish this or a comparable function.

Referring back to FIG. 8, the quantitative test results obtained by the testing system 18 are compared to prescribed norms. If the test results are within prescribed norms, the second operative sequence 66 issues an appropriate "Will Not Dispense Medication" message through the appropriate output devices 60/62. The normal test results are reported to the patient (via output devices 60/62) and, preferably, to the central facility 28 (via the modem 30) as well.

However, if the quantitative test results are not within prescribed norms, the second operative sequence 66 of the control element 50 proceeds with its further evaluation, taking into account still additional qualitative and quantitative considerations.

For example, should the patient complain of a fever, and the quantitative test results establish an above average temperature, the second operative sequence 66 may additionally prompt the patient, using the external output devices, with a series of questions relating to recent activities, such as exercise or eating, that may effect body temperature. The patient's responses are received and interpreted through the external input devices 56/58.

The second operative sequence 66 of the control element 50 compares and correlates this qualitative and quantitative information in accordance with preprogrammed diagnostic routines. If a correlation exists indicating that the patient has a temperature that is unrelated to recent activities, the second operative sequence 66 generates the second control signal 54 required to activate the second delivery mechanism 48 where the prescribed temperature reducing medication is stored.

In this situation, the second operative sequence 66 also preferable communicates with the patient with an appropriate "Can Dispense Medication" message (via the display 62 and with output speech device 60) and provides an advisory message to the central facility 28 using the modem 30.

In the preferred embodiment, the timing means 70 of the third operative sequence 68 is provided, along with the appropriate advisory message, to assure that symptom-specific medication is not administered too often.

If a correlation does not exist, or if a repeat administration is sought within a given time period, the patient is so informed by an appropriate "Will Not Administer Medication" message, and no medication is administered. However, an advisory message may nevertheless be transmitted to the central facility 28 or to a designated caregiver using the modem 30.

As shown in FIG. 3, the medication delivery system can separately store several different types of medication to treat different physical symptoms, such as high temperature, indigestion, or body pains. The control element 50 can receive and correlate the qualitative and quantitative information, and, upon arriving at a prescribed correlation, generate the specific control signal to administer the appropriate type of medication, depending upon the symptom encountered.

System for Altering Prescribed Medication Schedules For Remote Administration

In accordance with yet another aspect of the invention, the control element 50 can further include means for temporarily altering the routine dictated by a prescribed schedule stored in the internal memory 26 in response to a prescribed "Alter Routine" command received from either the patient or the central facility 28, or for permanently changing the medication administration schedule in response to a prescribed "Change Routine" command received from the central facility 28.

Figure 9A:
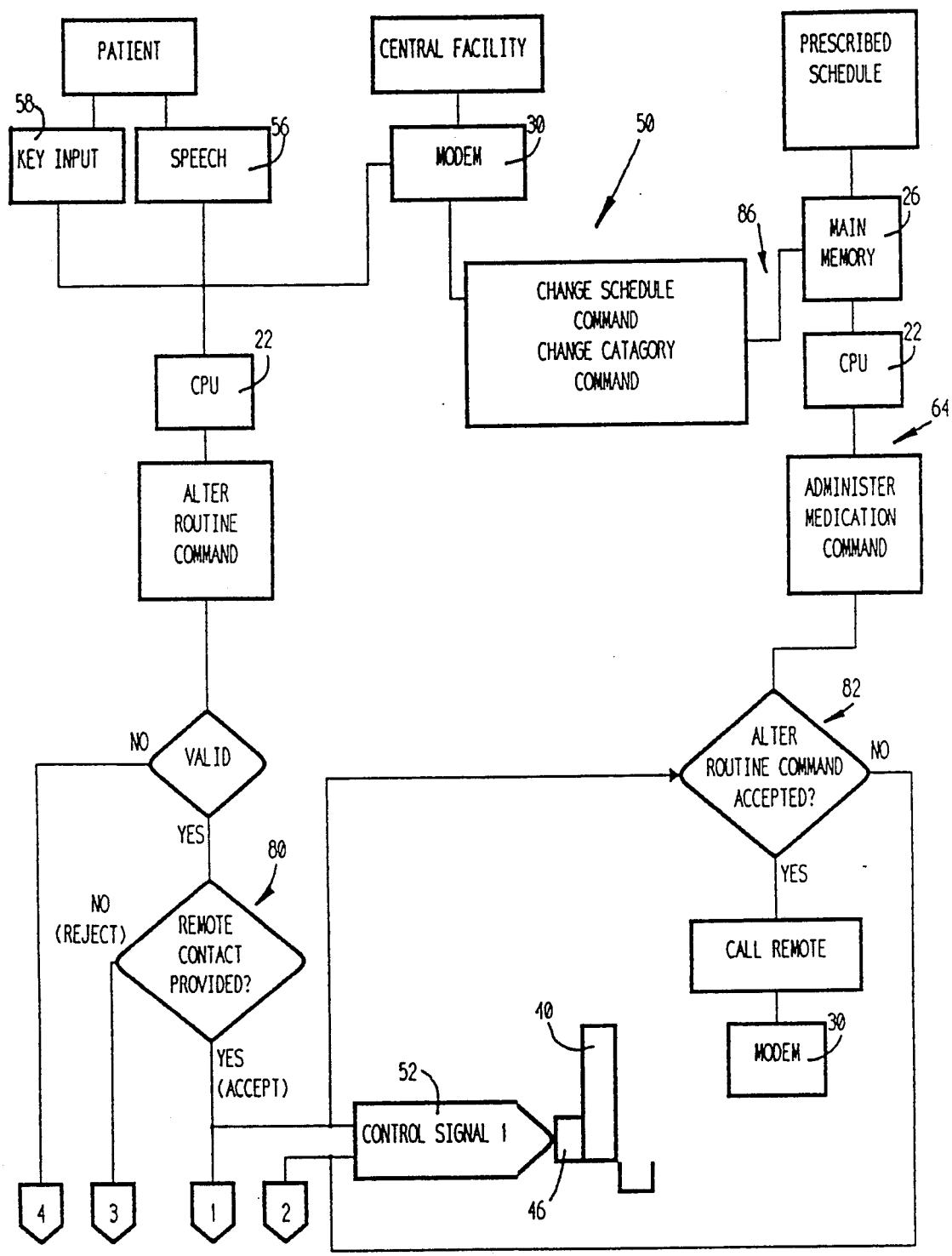
Figure 9B:
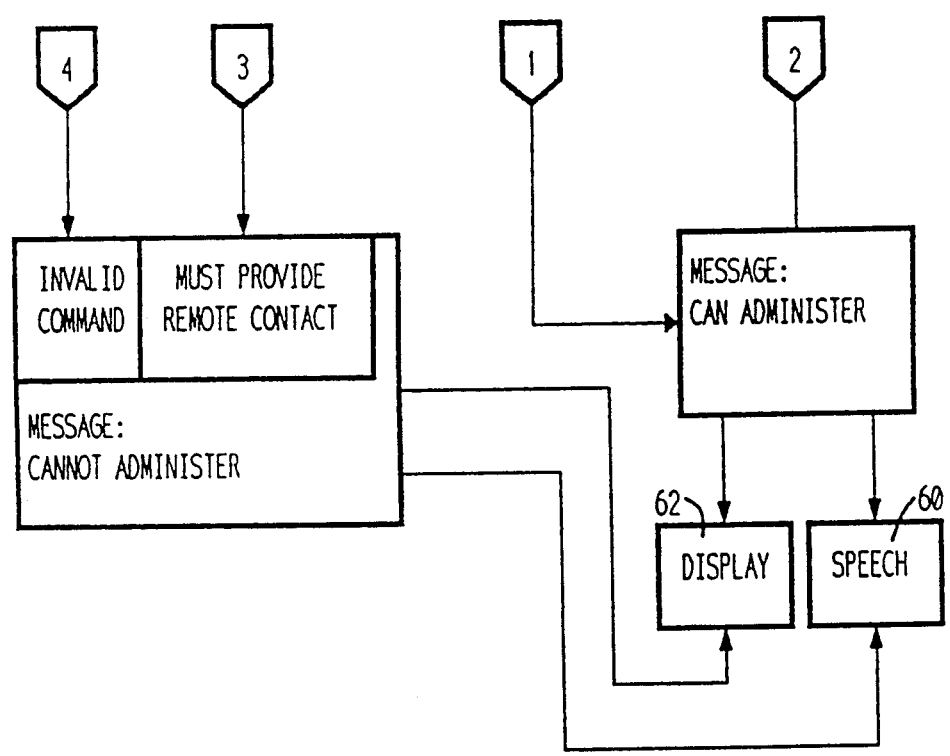
Figure 13:
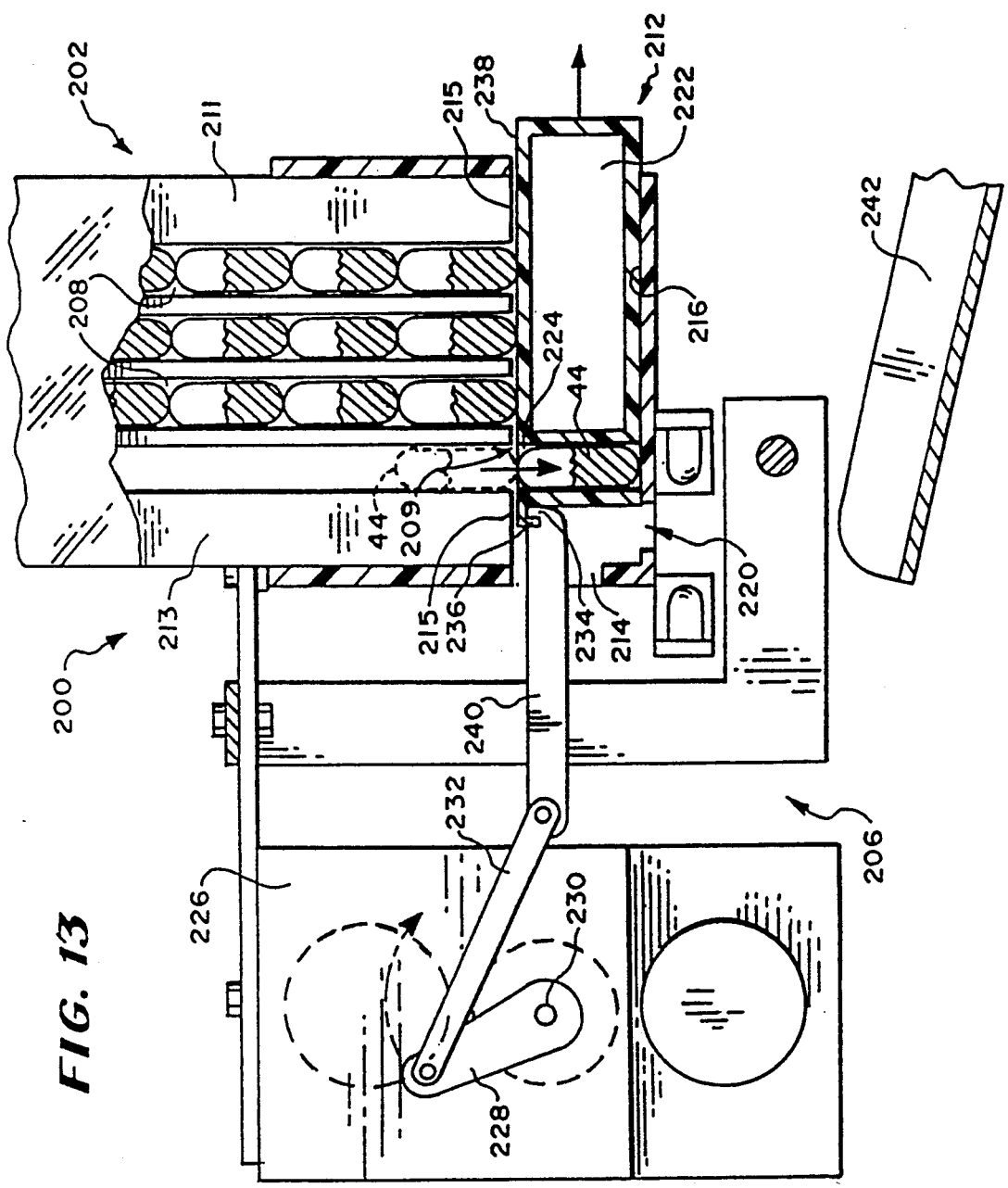

A control element 50 that serves this purpose is shown diagrammatically in FIG. 9. As before described, the control element 50 includes a first operative sequence 64, which bears the same reference numeral assigned before. The first operative sequence 64 administers medication in accordance with an internal signal generated according to a prescribed schedule contained in the main memory 26.

In this embodiment, the control element 50 comprises a fourth operative sequence 80 that alters the prescribed routine upon response to a prescribed "Alter Routine" command. The specific arrangement shown in FIG. 9 is based upon a representative situation where the patient will be away from home when a prescribed medication administration event is scheduled to occur. In this situation, the fourth operative sequence 80 serves to administer the medication in advance of the schedule, so that the patient can take the medication with him/her for administration at the prescribed time.

In a preferred arrangement, the fourth operative sequence 80 also serves to attempt affirmatively contact with the patient at his/her remote location (via path 84 in FIG. 9) when it is time to take the medication.

In this situation, the prescribed "Alter Routine" command may be issued either by the patient or by the central monitoring facility 28, according to the procedure prescribed by the attending physician. For example, the physician may order that only the central facility 28 can issue an "Alter Routine" command. In this arrangement, the fourth operative sequence 80 will not respond to an "Alter Routine" command issued directly by the patient. The patient would thereby be required to request an alteration in his/her routine from the physician or personnel at the central facility 28.

Upon receipt of a valid "Alter Routine" command, the fourth operative sequence 80 will, in the preferred arrangement shown in FIG. 9, require the patient to provide a phone number where he/she can be reached at the time the next prescribed medication event occurs. In this embodiment, the fourth operative sequence 80 will release the medication only if the remote contact information is provided by the patient. In an alternate arrangement, the fourth operative sequence 80 can release medication without requiring remote contact information.

In this arrangement, the fourth operative sequence 80 establishes a check point 82 within the routine of the first operative sequence 64. The check point 82 determines whether a valid "Alter Routine" command has been accepted by the fourth operative sequence 80. If it has, the first operative sequence 64 will respond to the prescribed schedule by generating a signal (via path 84 in FIG. 9) that does not administer medication, but attempts to contact the patient at the remote contact point using the modem 30. If contact is made, a message is transmitted to remind the patient that the prescribed time for taking the medication has arrived.

In one arrangement, the fourth operative sequence 80 can communicate with the away-from-home patient through a paging or cellular telephone system. Likewise, the patient can remotely communicate with the device when away from home.

In the "Alter Routine" sequence illustrated in FIG. 9, the fourth operative sequence 80 of the control element 50 does not alter the memory resident schedule itself. The prescribed schedule remains the same and controls during the next prescribed medication event, unless another "Alter Routine" command is accepted.

In the embodiment illustrated in FIG. 9, the control element includes a fifth operative sequence 86 to actually change the memory resident schedule in response to a valid "Change Schedule" command.

The specific arrangement shown in FIG. 9 is based upon a representative situation where the attending physician has changed the drug regime. The central monitoring facility 28 remotely issues a "Change Schedule" command to gain access to and alter the memory resident schedule. Preferable, a "Change Schedule" command will be received and interpreted by the system only with appropriate pass word precautions and safeguards.

In the same manner, the attending physician can by issuing a prescribed "Change Category" command to change the administration criteria of medication retained by the system. For example, the physicians can remotely make a medication that could be administered "on demand" to a "schedule only" category, and vice versa.

A Representative Physical Embodiment

The specific configuration of the interactive medication delivery system 20 as above described can vary according to the form in which the medication is administered. For example, one or more types of medication can be administered in predetermined dosages in sealed packets or "blister packs". Alternatively, or in combination, single dosages of a medication can be administered in a pill or caplet form, either in unsealed, "loose" form or on sealed rolls.

Attention is directed to FIGS. 1 to 3 and 10 to 16, where a representative system 200 for storing and delivering individual pills or caplets is shown that embodies the features of the invention.

The system 200, is carried within the confines of the patient monitoring and assistance device 10 (see FIGS. 1 to 3). The system 200 includes discrete medication storage compartments 202 A through J (see FIG. 3). The storage compartments 202 are each capable of separately storing medication in pill or caplet form.

In the illustrated embodiment shown in FIG. 3, there are ten storage compartments 202 located within an enclosed housing. Of course, the number of individual compartments can vary according to the needs of the patient. Each compartment 202 is capable of holding a number of individual pills/caplets (designated by reference numeral 44 in FIG. 3). The number of pills/caplets carried within each compartment 202 is determined by the physician according to the demands of the particular medication regime and how often the medication is to be replenished. Typically, a two week supply of medication can be contained within each compartment 202.

As shown in FIG. 3, the pills/caplets 44 are arranged side-by-side in a plurality of vertically stacked columns 208 within each compartment 202. As shown in FIG. 3, the compartments 202 preferably differ in overall vertical height and/or transverse thickness. The differing physical size of the compartments 202 (particularly in terms of thickness) permits the storage of pills/caplets of differing sizes. It also assures the proper ordered arrangement of the compartments 202 within the system 200, as will be described in greater detail later.

The housing 204 that encloses the compartments 202 is mounted in the device 10, behind the drawer 38 that contains the testing devices (see FIGS. 10 and 11). The housing 204 can be tilted out from back of the device 10 for service and to load medication into the system 200 (see FIG. 2 also).

In the illustrated embodiment, as best seen in FIG. 3, the system 200 includes ten separate medication delivery means or mechanisms 206 A through J, one associated with each storage compartment 202. Each mechanism 206 is individually controlled by one of the control elements 50 in response to a prescribed control signal or signals in the manner previously described.

Each delivery mechanism 206 is identical in construction, so only one will be described in detail.

In the illustrated arrangement (as best shown in FIGS. 12 to 15), the medication storage columns 208 are located between a front (right) wall 211 and a rear (left) wall 213 formed within the compartment 202. The lower end 209 of each vertical medication storage column 208 is open. The ends 209 open into a channel 210 that spans the bottom of the compartment 202. The lower edges 215 of the front and rear walls 211 and 213 are closed.

The channel 210 includes an open front end 212 adjacent the compartment's front wall 211 and an open back end 214 adjacent the compartment's rear wall 213 (respectively positioned to the right and to the left in FIGS. 12 to 15). The channel 210 also includes a bottom wall 216 and two upstanding sidewalls 218 (see FIG. 3). The channel bottom wall 216 includes a opening 220 adjacent its open back (left) end 214, directly beneath the closed lower edge 215 of the compartment's rear wall 213.

Figure 14:
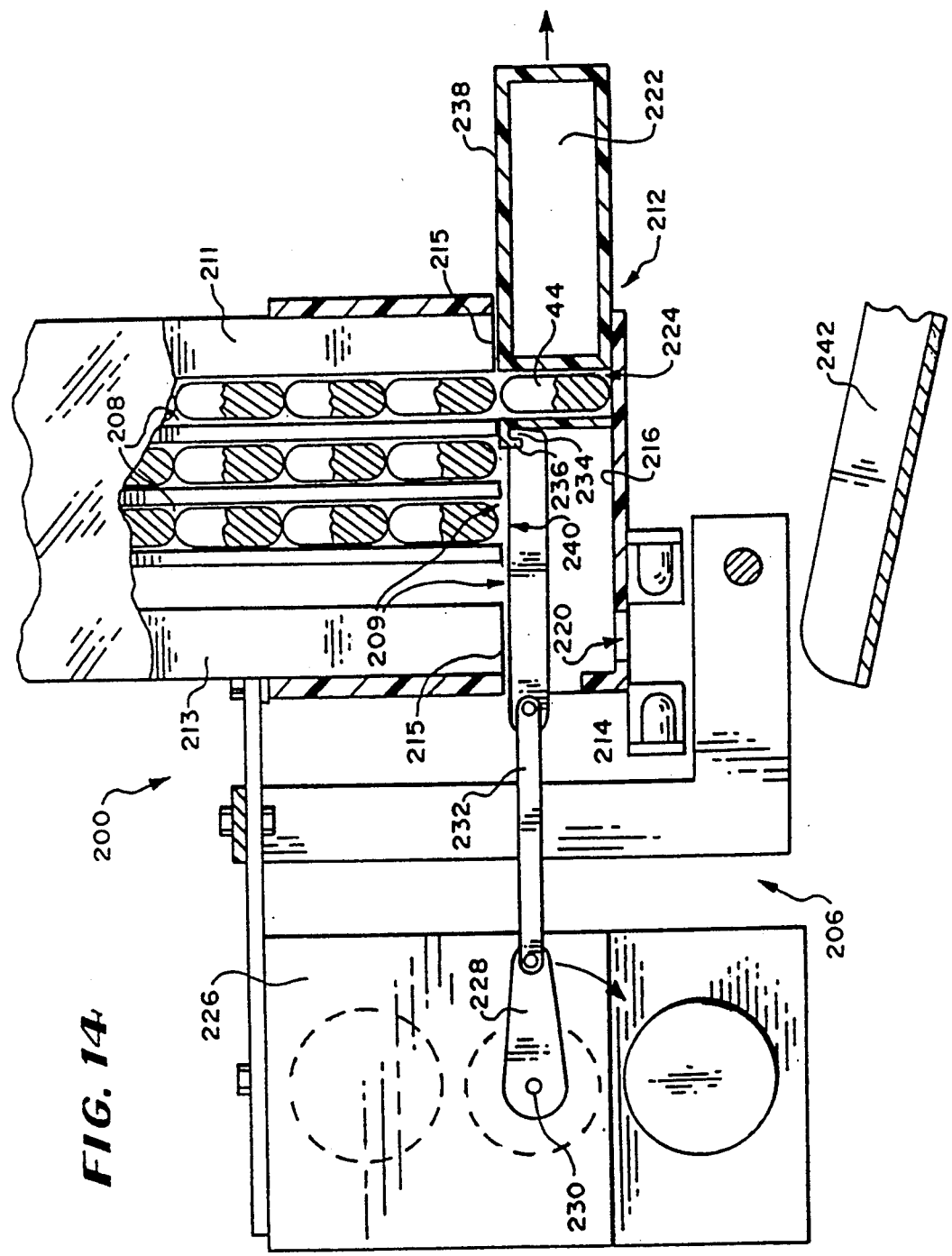

The delivery mechanism includes a shuttle member 222 that is movable within the channel 210 between a rearward position, fully within the channel 210 (shown in FIG. 12), and a forward position, extending partially outside the open front end 212 of the channel 210 (shown in FIGS. 3 and 14).

The shuttle member 222 includes an open passageway 224 that registers with the bottom opening 220 in the channel 210 when the shuttle member 222 is in its rearward position (see FIG. 12). Movement of the shuttle member 222 successively toward the forward position (see FIGS. 13 and 14) brings the passageway 224 into sequential registration with the open bottom 209 of each of the storage columns 208.

A linkage assembly couples each shuttle member 222 to an associated electric motor 226 to drive the shuttle member 222 laterally forward and backward within the channel 210. While the construction of the linkage assembly may vary, in the illustrated embodiment, it includes a rotating crank 228 coupled to the drive shaft 230 of the associated motor 226. A double pivoted link 232 is attached at one end to the crank 228. The other end of the double pivoted link 232 includes a hook 234 that attaches to a lip 236 on the end wall of the shuttle member 222.

Rotation of crank 228 thereby imparts forward and rearward pivotal movement to the shuttle member 222. In particular, as shown in FIGS. 12 to 15, one full revolution (360-degrees) of the crank 228 will cycle the shuttle member 222 from its rearward position (FIG. 12) into its forward position (FIG. 14) and back to its rearward position (FIG. 15).

As the shuttle member 222 is moved out toward its forward position (see FIG. 12), the passageway 224 will successively come into and out of registry with the bottom 209 of each storage column 208 beginning with the rearwardmost (farthest left) column. The first bottommost pill/caplet encountered in a column will fall by gravity into the empty passageway 224. The closed bottom 216 of the channel 210 retains the fallen pill/caplet within the passageway 224 as the shuttle member 222 moves into is fully forward position and back toward its rearward position (in which the passageway is located beneath the closed lower edge 215 of the compartment's rear wall 213). The presence of the retained pill/caplet prevents another pill/caplet from falling into the passageway 224. Likewise, the leading top wall portion 238 of the shuttle member 222 and the trailing top portion 240 of the link 232 serve to progressively close the bottoms of the other columns as the shuttle member 222 is advanced, preventing additional pills/caplets from entering the channel 210.

When the shuttle member 222 returns to the rearward position (see FIG. 15), the passageway 224 will again register with the bottom channel opening 220. The retained pill/caplet will fall from the passageway 224 through the bottom channel opening 220 and then into a delivery chute 242 that leads to a medication dispenser 244 at the front of the device 10 (see FIG. 3 also).

As shown in FIGS. 1 and 2, the medication dispenser 244 is movable between a closed position (FIG. 1) and an opened position (FIG. 2). A spring 245 (see FIG. 3) normally biases the dispenser 244 toward the opened position, and a solenoid controlled latching mechanism 247 is provided to lock the dispenser 244 in the closed position. At the time medication is released into the delivery chute 242, the dispenser 244 is located in its locked and closed position. Upon delivery of the medication to the dispenser 244, a signal to the latching mechanism 247 allows the dispenser 244 to move into its opened position in response to the bias of the spring 245. The dispensed medication is thereby made available to the patient. Upon taking the medication, the patient closes the dispenser 244, preferably in response to a prompt generated by the device 200.

As in the previously described embodiment, in the illustrated and preferred embodiment of this system (see FIG. 10), each compartment 202 can be individually removed from the housing 204 as a module for replenishment of the medication when the housing 204 is tilted through the back of the device 10. The removable, interchangeable modular design of the compartments 202 simplifies a change in medication brought about by a change in the prescribed medication regime.

Again, it is contemplated that the modular compartments 202 will be prepacked by trained medical or pharmacy personnel at a location away from the device 10 and then carried on site.

In the illustrated arrangement shown in FIG. 10, the motors and linkage assemblies remain in the housing 204 upon removal of the compartments 202. The hooked end 234 of the pivoted link 232 is readily engaged and disengaged from the lip 236 of the associated shuttle member 222.

The housing 204 includes slots 250 arranged to receive and retain the compartments 202 in proper alignment with the associated linkage assembly (see FIG. 16). The slots 250, like the compartments 202, differ in size, so that a given compartment 202 will uniquely physically fit into only a selected one of the slots 250. This assures the desired ordered arrangement of medication within the dispensing system 200.

In the illustrated and preferred embodiment (see FIG. 16), each compartment 202 is uniquely identified using machine readable code 252. In the illustrated embodiment, the code 252 is readable by an optical scanning system 254 associated with each slot. The code 252 contains information about the medication carried within the associated compartment 202, such as the type of medication, the number of dosages contained, and the patient's name or prescription number. The scanning system 254 reads the code 252 as the compartment 202 is inserted into the appropriate fitted slot 250.

As shown in FIG. 16, the control element 50 for the dispensing system 200 preferably includes a comparator 256 that compares the information sensed by the scanning system 254 with an expected result carried in the main memory 26. If the sensed information is not the expected result—for example, when the medication for the wrong patient is being accidentally loaded into the system 200—an appropriate error message is generated.

The system 200 thus assures, in fail-safe fashion, the placement of the prescribed medication for administration to the patient.

The system 200 shown in FIGS. 1 to 3 and 10 to 16 includes the separate medication compartments and ten individually controllable delivery mechanisms, one for each compartment. The system 200 can include any one of the control elements 50 shown in FIGS. 6 to 9. The selected control element 50 serves to individually activate the motors 226 associated with each of the compartments 202 by generating different control signals in response to different input criteria in the manner previously described.

For example, if a medication regime requires the administration of three different pills/caplets according to a prescribed schedule, the control element 50 associated with the system 200 can simultaneously generate a first control signal to each of the delivery mechanisms associated with the particular compartments in which the prescribed pills/caplets are located. The three pills/caplets would therefore be dispensed sequentially or at the same time. The control element 50 could dispense other pills/caplets according to different prescribed schedules, or upon patient demands, upon the issuance of appropriate control signals to the other delivery mechanisms.

The system 200 shown in FIGS. 1 to 3 and 10 to 16 is thereby capable of storing and coordinating the administration of many different categories of medication in pill or caplet form in accordance with one or more prescribed schedules, upon demand, or upon any other selected administration criteria.

Associated System for Maintaining and Managing a Medication Inventory

In accordance with another aspect of the invention, the medication delivery system 20 as above described forms a part of an overall system 100 that inventories and otherwise manages the medication regime of a patient. This system 100 is shown in FIG. 17. As there shown, the inventory and management system 100 can be maintained in the mass storage system at the central monitoring facility 28, or within on-site internal memory 26, or (preferably) at both locations.

The inventory and management system 100 can network the central monitoring facility 28 with the medical delivery systems (designated 20A, 20B, and 20C in FIG. 17) of a number of patients, thereby centralizing inventory and management control over the medication regimes of different patients.

The inventory management system 100 maintains a log 102A/B/C for each medication delivery system 20A/B/C in the network. Each log 102A/B/C is preferably maintained on site by each delivery system 20A/B/C/ as well at the central monitoring facility. While the contents of each log 102A/B/C will differ, the basic format of each is the same. Therefore, only one (log 102A) will be described As shown in FIG. 18, the log 102 includes a separate data file for each medication storage compartment in the associated system 20, either in sequential or random access format. In FIG. 18, two medication storage compartments 40 and 42 are shown for illustration purposes (as in FIG. 7), and there are thus two associated data files 104 and 106. Each file 104 and 106 includes a number of records, which contains the information necessary to oversee and manage the administration of the particular medication stored in the associated compartment. These records are generally identified in FIG. 18 as R1, R2, R3, etc.

In the illustrated embodiment, each medication file 104 and 106 includes a first record (R1) 108 that reflects the date and time the medication was administered according to the schedule in internal memory 26; a second record (R2) 110 that reflects the date and time the medication was administered on demand; and a third record (R3) 112 that reflects the date and time the system 20 refused to administer medication.

Each medication file 104 and 106 also includes a fourth record (R4) 114 that contains a number that represents the amount of the medication presently remaining within the associated storage compartment 40/42.

Each medication file 104 and 106 can include a number of additional records depending upon the level of detail required. For example, the medication file can include a record that reflects the category of the medication as programmed in the control element 50 (by schedule, on demand, or both); the minimum dosage interval programmed in the timing means 70 (see FIG. 8); the prescribed dosage in terms of time and amount programed in internal memory 26; the storage compartment number where the medication is located within the delivery system 20; and the date on which the storage compartment was last replenished.

The first, second, third, and fourth records 108/110/112/114 are created and updated based upon signals generated by the associated control element 50. In FIG. 18, the control element 50 shown in FIG. 7 is contemplated.

The generation of the first control signal 52 and accompanying "Can Administer" message loads date/time data into and updates the first record 108 of both files 104 and 106 (it is assumed that the medications contained in compartments 40 and 42 are each administered according to the schedule).

The generation of the second control signal 54 and accompanying "Can Administer" message loads date/time data into and updates the second record 110 of the second file 106 (it is assumed that only the medication contained in the second compartment 42 can be administered upon demand).

The generation of a "Cannot Administer" message loads date/time data into and updates the third record 112 of each file 104/106.

The fourth record 114 of each file 104/106 is initialized each time the medication in the associated storage compartment 40/42 is replenished on site, to thereby represent the amount of medication initially placed inside the compartment 40/42. In the illustrated embodiment, it is contemplated that the person who replenishes the medication on-site will manually initialize the fourth record 114 through an appropriate entry made using the input keys 58. Of course, the initialization can be manually made, via the modem 30, from the central facility 28. The initialization could also be accomplished automatically when the compartment 40/42 is loaded into the system 20, by using the machine readable code and associated scanning device previously described.

Once initialized, the fourth record 114 of each file 104/106 is updated by reducing the initialized amount by one whenever a first or second control signal 52 and 54 is generated, as appropriate.

In the illustrated and preferred embodiment (see FIG. 18), the system 100 also includes a comparator 116 associated with each medication file 104/106. Each time the fourth record 114 is updated and/or at prescribed periodic time intervals, the comparator 116 compares the number stored in the fourth record 114 with a preselected number stored in the main memory 26 that represents a minimum storage amount for that particular storage compartment. When the number stored in the fourth record 114 is equal to or less than the associated minimum storage amount, a "Replenish" signal is generated to alert the patient and the central monitoring facility 28. A person is then sent to replenish the medication contained in the associated compartment 40/42 and to initialize the fourth record 114.

The system 100 thus continuously monitors the patient's medication regime and assures that medication sufficient to comply with the regime is available within the medication delivery system 20.

As shown in FIG. 19, the system 100 preferably also includes a follow up sequence 118 for determining whether medication that is dispensed is actually taken by the patient. In the illustrated embodiment, the follow up sequence 118 comprises a loop 120 that, after the medication is dispensed, inquires whether the dispensed medication was taken. The inquiry is made either through the speech output device 60 or the display 62, or both. The loop 120 will periodically repeat the inquiry unless either an affirmative or negative response is provided by the patient, either by a voice command or through the input keys.

If an affirmative response is received, the appropriate first or second record 108/110 is updated to reflect that the medication dispensed was actually taken.

If a negative response is received, the follow up sequence 118 will first determine whether the patient accidentally lost the dispensed medication through an additional series of inquiries by voice and/or display.

The follow up sequence may inquire "Did you lose the medication? "If the patient's response (by voice or by input key) indicates that the medication was dropped and lost, the appropriate first and second record 108/112 is updated to reflect this fact. In this instance, the central facility 28 is alerted. The central facility 28 may then investigate and issue the appropriate "Repeat Administration" command to administer a repeat dose of the lost medication. The "Repeat Administration" command overrides any associated timing means 80.

If the patient will not respond, the follow up sequence 118 may warn the patient "If you do not take you medication within three minutes, I shall notify the central facility" and wait three minutes for an affirmative response. If the affirmative response is not received, the appropriate first or second record 108/110 is updated accordingly. The central facility 28 is also alerted via the modem 30 that the patient has failed to take the dispensed medication. The central facility 28 will then investigate.

It should be appreciated that all of the medication delivery systems described in this Specification are applicable for use out of association with a patient monitoring and assistance device. The systems can be used in virtually any environment where storage and delivery of selective medications are desired, such as in a hospital, nursing home, or pharmacy. It should also be appreciated that the medication delivery systems described can be actuated and controlled manually, without reliance upon the automated and highly interactive microprocessor controlled systems described in this Specification. Furthermore, each delivery mechanism and associated storage compartment can be used individually as a single unit, as well as in the multiple configurations shown in this Specification.

The features of the many aspects of the invention are set forth in the following claims.

We claim:

1. A medication delivery system comprising
a housing
first storage means for storing at least one dose of a medication within the housing away from access by the patient,
second storage means separate from the first storage means for storing at least one dose of a medication within the housing away from access by the patient,
first delivery means associated with the first storage means for selectively delivering a medication dose from the first storage means to the patient,
second delivery means associated with the second storage means for selectively delivering a medication dose from the second storage means to the patient,
internal memory means for storing a prescribed schedule for administering medication,
external input means for receiving and interpreting at least one prescribed medication delivery command from the patient,
first control means for generating a command signal to actuate the first delivery means in response to the prescribed schedule stored in the internal memory means and not in response to receipt of a medication delivery command from the external input means including first means for generating an error signal refusing to administer medication whenever invalid input is received from the patient,
second control means for generating a command signal to actuate the second delivery means in response to the receipt of a prescribed medication delivery command from the external input means, and
means operative in response to the command signals generated by the control means for maintaining a data file for each medication dispensing device, the data file including a record representing a running total of the number of medication dosages contained in the associated storage compartment, the data file including a record reflecting the administration of medication according to the prescribed schedule, a record reflecting he administration of medication in response to the medication delivery command from the patient, and a record indicating the generation of the error signal.

2. A system according to claim 1 wherein the record is initialized each time the associated storage compartment is replenished to represent the number of medication dosages loaded into the compartment, and wherein each command signal actuating the associated delivery mechanism updates the record by subtracting one from the number contained in the record.

3. A system according to claim 1 or 2 and further including a comparator for comparing the number contained in the record with a predetermined minimum value and for generating a signal when the number is equal to or less than the minimum value.

4. A system according to claim 1 and further including second external input means for receiving and interpreting at least one change medication schedule command from the patient, and further including means for altering the prescribed schedule stored in the internal memory means in response to the receipt of a prescribed change medication schedule command from the second input means.

5. A system according to claim 4 wherein the second external input means includes speech recognition means for receiving and interpreting at least one prescribed verbal response made by the patient.

6. A system according to claim 1 wherein the second control means includes timing means for preventing a second actuation of the second delivery means when the time period between a first and second actuation is less than a prescribed period, and second means for generating a second error signal refusing to administer medication whenever the timing means prevents a second actuation of the second delivery means, and wherein the data file includes a record indicating the generation of the second error signal.

7. A system according to claim 1 wherein the external input means includes speech recognition means for receiving and interpreting at least one prescribed verbal response made by the patient.

* * * * *